United States Patent
Cichocki, Jr. et al.

(10) Patent No.: US 11,272,923 B2
(45) Date of Patent: Mar. 15, 2022

(54) SYSTEMS, DEVICES AND METHODS FOR SECURING SUTURES TO SURGICAL NEEDLES MADE OF SUPERELASTIC MATERIALS

(71) Applicant: Ethicon, Inc., Somerville, NJ (US)

(72) Inventors: Frank Richard Cichocki, Jr., Easton, PA (US); Christophe Vailhe, Hillsborough, NJ (US); Thomas Nering, Milford, NJ (US); Alexander M. Cannara, Roseland, NJ (US); Duan Li Ou, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 49 days.

(21) Appl. No.: 16/282,580

(22) Filed: Feb. 22, 2019

(65) Prior Publication Data
US 2020/0268375 A1    Aug. 27, 2020

(51) Int. Cl.
*A61B 17/06*    (2006.01)
*A61B 17/00*    (2006.01)

(52) U.S. Cl.
CPC .. *A61B 17/06004* (2013.01); *A61B 17/06066* (2013.01); *A61B 17/06166* (2013.01); *A61B 2017/00477* (2013.01); *A61B 2017/00867* (2013.01); *A61B 2017/0608* (2013.01); *A61B 2017/06028* (2013.01)

(58) Field of Classification Search
CPC ........... A61B 2017/06028; A61B 2017/06033; A61B 2017/06038; A61B 2017/06042; A61B 2017/06047; A61B 17/06004
See application file for complete search history.

(56) References Cited

U.S. PATENT DOCUMENTS

| 1,960,117 A | 5/1934 | Lydeard |
| 2,302,986 A | 1/1946 | Vollrath |
| 2,591,063 A | 4/1952 | Goldberg |
| 3,125,095 A | 3/1964 | Kaufman et al. |
| 3,130,728 A | 4/1964 | Pearson et al. |

(Continued)

FOREIGN PATENT DOCUMENTS

| CH | 597835 | 4/1978 |
| DE | 3223153 | 8/1983 |

(Continued)

OTHER PUBLICATIONS

International Search Report issued in corresponding International Application No. PCT/IB2020/051381, dated May 29, 2020, 4 pages.

*Primary Examiner* — Melanie R Tyson
*Assistant Examiner* — Mohammed S Adam

(57) ABSTRACT

A needle and suture assembly includes a needle made of a superelastic alloy, such as Nitinol, including an elongated body having a proximal end and a distal end with a sharpened tip, a suture having a free end juxtaposed with the proximal end of the elongated body of the needle, and a connector disposed between the needle and the suture. The connector includes a first end attached to the proximal end of the elongated body of the needle and a second end attached to the free end of the suture. The connector is made of a material, such as stainless steel, having less elasticity and greater plasticity than the superelastic alloy of the needle.

17 Claims, 20 Drawing Sheets

(56) References Cited

U.S. PATENT DOCUMENTS

| | | | |
|---|---|---|---|
| 3,152,591 A | | 10/1964 | King |
| 3,311,110 A | | 3/1967 | Singerman et al. |
| 4,060,885 A | | 12/1977 | Hoffman et al. |
| 4,359,053 A | | 11/1982 | Benjamin |
| 4,926,860 A | | 5/1990 | Stice et al. |
| 5,084,063 A | | 1/1992 | Korthoff |
| 5,116,358 A | | 5/1992 | Granger |
| 5,139,514 A | * | 8/1992 | Korthoff .......... A61B 17/06004 606/223 |
| 5,226,912 A | | 7/1993 | Kaplan et al. |
| 5,306,288 A | | 4/1994 | Granger et al. |
| 5,358,498 A | | 10/1994 | Shave |
| 10,260,135 B2 | † | 4/2019 | Loubens |
| 2016/0022264 A1 | * | 1/2016 | Matsutani ........ A61B 17/06066 606/225 |
| 2017/0049439 A1 | | 2/2017 | Keyser et al. |
| 2019/0059882 A1 | * | 2/2019 | Yoshimi ............. A61B 17/0469 |

FOREIGN PATENT DOCUMENTS

| | | |
|---|---|---|
| DE | 4220283 | 12/1993 |
| EP | 444777 | 9/1991 |
| EP | 2286732 | 2/2011 |
| EP | 3431014 | 1/2019 |
| JP | 11276492 | 10/1999 |
| WO | 2014071477 | 5/2014 |

\* cited by examiner
† cited by third party

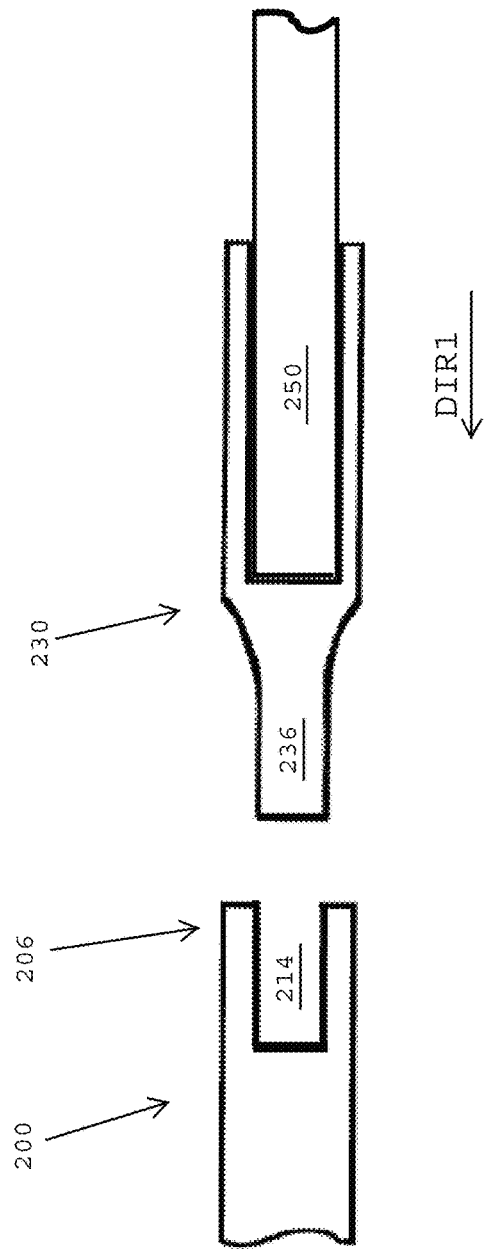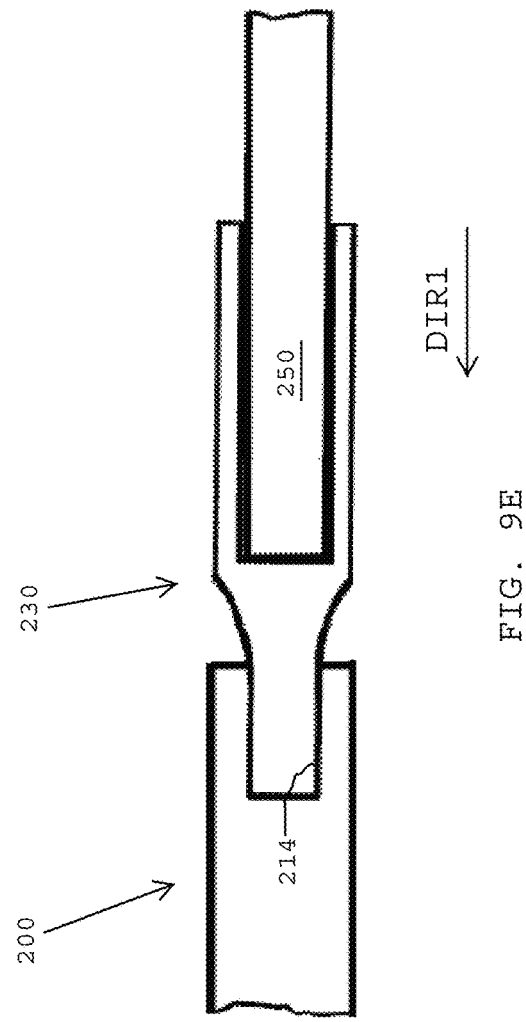

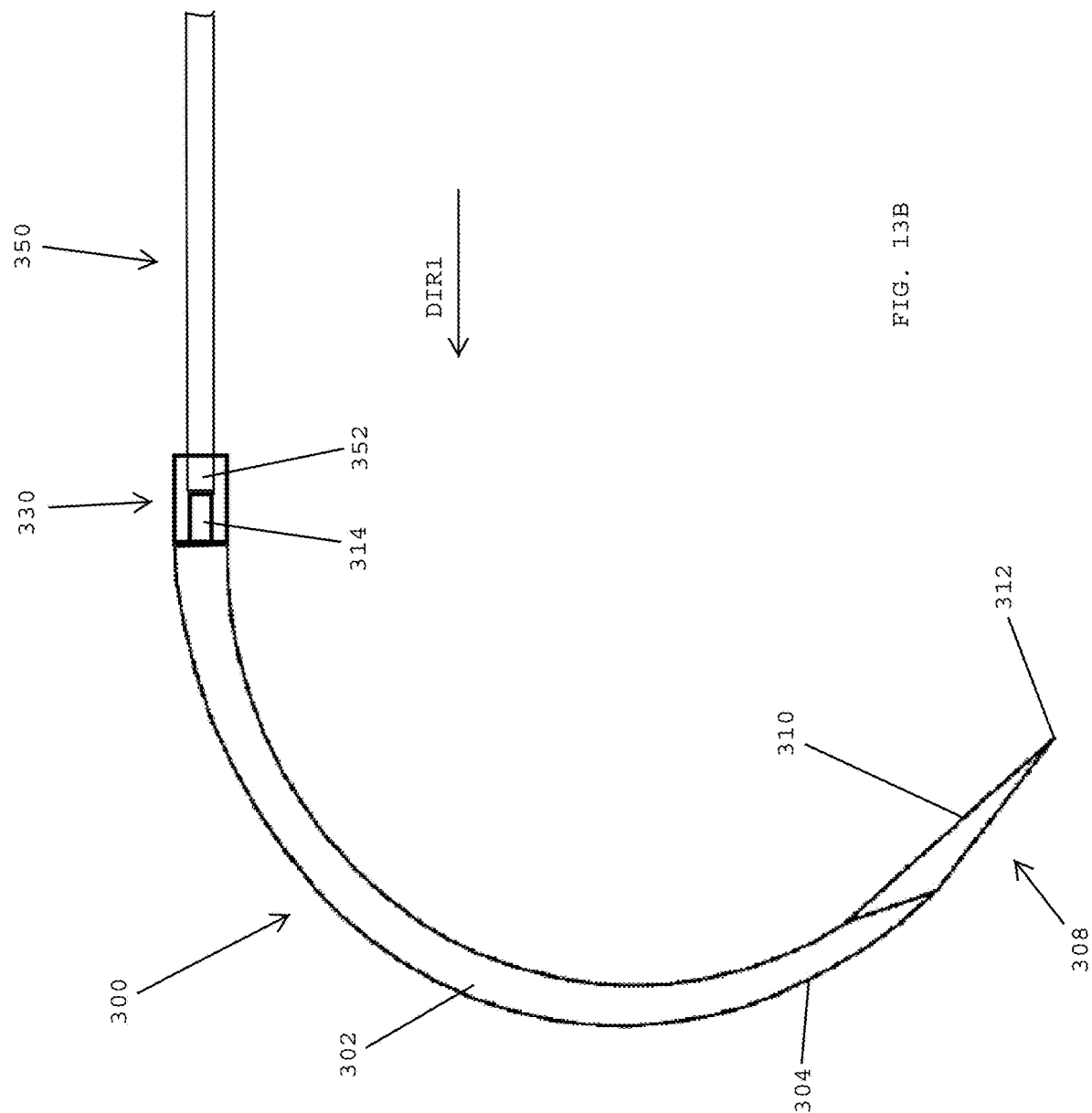

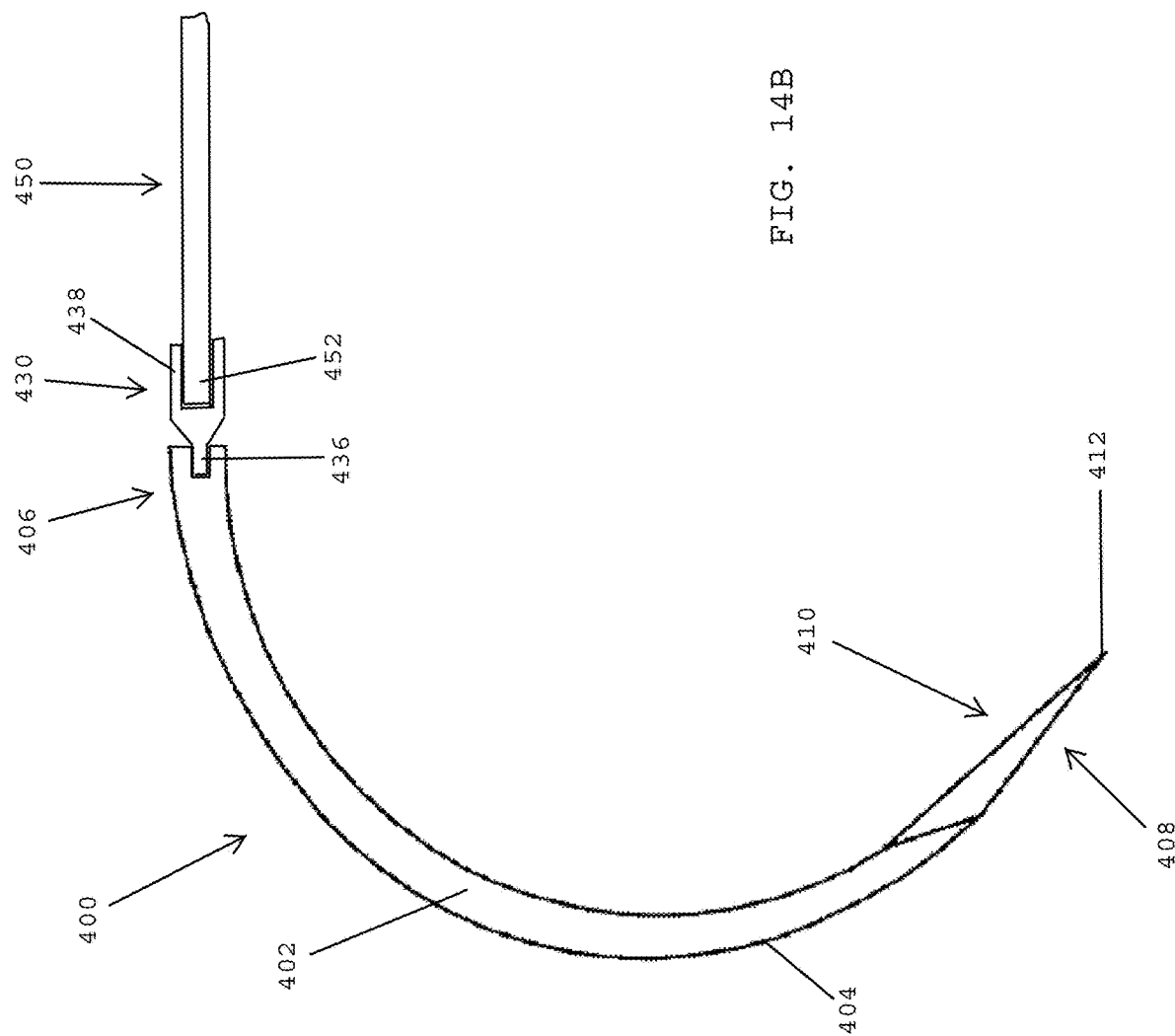

SYSTEMS, DEVICES AND METHODS FOR SECURING SUTURES TO SURGICAL NEEDLES MADE OF SUPERELASTIC MATERIALS

BACKGROUND OF THE INVENTION

Field of the Invention

The present patent application is generally related to suturing tissue, and is more specifically related to systems, devices and methods for securing sutures to surgical needles.

Description of the Related Art

Sutures are used to approximate tissue that has been separated during a surgical procedure or due to an accident or trauma. Instruments used for suturing typically include a needle and a trailing length of suture material that is attached to an end of the needle. Over the years, the materials and techniques used to attach sutures to needles have been improved to the point whereby many surgical needle and suture assemblies are manufactured using state of the art metal and polymer sciences.

Armed surgical needles, i.e., needles having sutures attached to one end thereof, are typically manufactured utilizing manual, semi-automated, and fully automated procedures that feed a length of suture material into a suture receiving bore (e.g., a hole) of a surgical needle, and that swage (i.e., compress) a part of the surgical needle to the end of the suture.

Methods for swaging needles to sutures typically involve inserting the free end of a suture into a suture receiving bore of a needle barrel of a surgical needle, and holding the suture inside the bore while a swage die impinges upon the outer surface of the needle barrel, thereby compressing a portion of the bore onto the suture. The compressed portion of the suture receiving bore grasps the suture by mechanical interference and by surface friction. The swaging process is conducted to create a reliable attachment between the needle barrel and the suture that meets or exceeds "pull-out" strength standards.

In order to minimize patient trauma during minimally invasive surgical procedures, many efforts have been directed to reducing the size (e.g., diameter) of the cannulas and trocars that are inserted into patients. When a surgical procedure requires suturing tissue, a problem arises in the types of needle and suture assemblies that can be delivered through the cannula to the surgical site. Many surgeons prefer to use curved needles, which are typically in the range of ¼ to ⅝ of a circle (i.e., an arc whose interior angle is in the range of about 90 degrees-225 degrees). Curved needles having these dimensions require the cannula to be large enough to accommodate the arc of the needle, which in many procedures is not feasible because the preferred curved surgical needle cannot pass through the preferred, narrower, cannula to the surgical site.

In an effort to resolve the above-noted size problems, advances have been made to provide surgical needles made of superelastic alloys that elastically deflect or straighten when passed through a cannula and then return back to the original curved shape when removed from the cannula at the surgical site.

One well-known superelastic alloy used to make needles having superelastic properties is the Ni—Ti alloy, which is commonly referred to as Nitinol. The superelastic properties are due to a stress-induced martensitic phase change that takes place in certain alloys above their transformation temperature. The martensite reverts immediately to undeformed austenite as soon as the stress is removed providing a very springy "rubberlike" elasticity in these alloys.

A needle produced from a superelastic alloy exhibiting a curvature much larger than can be normally accommodated by a small diameter cannula can flex into a predominantly straight shape as it is pushed through the small cannula into the surgical site. After the needle has passed through the cannula and reaches the surgical site, the superelastic properties present in the needles will return the needle back to its original curved configuration.

At present, almost all disposable needles are attached to sutures using a bore or hole at the end of the barrel, which is plastically deformed during swaging to compress and attach the suture to the needle. With the development of the superelastic alloy needles discussed above for improved control, however, the plasticity of needles has been reduced to a minimum, which has led to the development of a number of challenges when seeking to attach sutures to needles via conventional swaging processes that depend on plastic deformation at the attachment site.

For example, in many instances, the attachment feature on the needle is tailored for a certain suture size and the strength of the attachment depends upon the outer diameter of the suture. In addition, certain suture materials are more sensitive to over-compression than other suture materials, which makes it difficult to use one attachment system for different sutures. Moreover, minimally invasive surgical (MIS) techniques that require surgical needles to be passed through trocars further maximize the need to form reliable attachments between sutures and suture needles.

Relative to stainless steel needles, the needle pull off (NPO) force for sutures mechanically attached to surgical needles made of superelastic materials (e.g., Nitinol needles) is low. The low NPO is due to the spring back of the barrel of the needle that occurs immediately after a swage strike due to the superelastic properties of the needle. Thus, superelastic needle barrels and nitinol needle barrels are intrinsically problematic for swage attachment of sutures. This may risk patient harm due to lost needles or even projectile detachment as the needle passes through a cannula.

Thus, there is a need for improved systems, devices and methods for forming stronger, more reliable and consistent attachment of sutures to surgical needles made of superelastic alloys and surgical needles having shape memory properties.

SUMMARY OF THE INVENTION

In one embodiment, a needle and suture assembly preferably includes a needle made of a superelastic alloy, such as Nitinol. In one embodiment, the needle has an elongated body including a proximal end and a distal end with a sharpened tip. In one embodiment, a suture has a free end juxtaposed with the proximal end of the elongated body of the needle, and a connector is disposed between the needle and the suture. In one embodiment, the connector desirably includes a first end attached to the proximal end of the elongated body of the needle and a second end attached to the free end of the suture.

In one embodiment, the connector is made of a material having greater plasticity than the superelastic alloy of the needle. In one embodiment, the connector is made of stainless steel, such as austenitic stainless steel or 316 stainless steel.

In one embodiment, the needle is made of a material having greater elasticity than the connector. In one embodiment, the needle may be curved. In one embodiment, the needle may be straight. In one embodiment, the needle may be a curved suture needle that is designed to flatten or straighten for passing through a trocar (e.g., a 5 mm trocar) that has a smaller inner diameter than the undeflected height of the curved needle.

In one embodiment, the needle preferably includes an attachment post projecting from the proximal end of the elongated body. In one embodiment, the elongated body of the needle has a first cross-sectional diameter and the attachment post has a second cross-sectional diameter that is smaller than the first cross-sectional diameter of the elongated body.

In one embodiment, the attachment post preferably includes a distal end secured to a proximal end face of the elongated body and a proximal end spaced from the distal end of the attachment post that defines a proximal-most end of the needle. In one embodiment, the distal end of the attachment post has a first outer diameter, and the proximal end of the attachment post has a second outer diameter that is greater than the first outer diameter at the distal end of the attachment post. In one embodiment, the attachment post has a lateral surface that extends along a length of the attachment post and that slopes inwardly between the proximal end and the distal end of the attachment post.

In one embodiment, the connector preferably includes a tubular body having a conduit that extends from a first opening at a first end of the tubular body to a second opening at a second end of the tubular body.

In one embodiment, the attachment post is inserted into the first opening at the first end of the tubular body and extends into the conduit for securing the tubular body with the attachment post of the needle.

In one embodiment, the free end of the suture is inserted into the second opening at the second end of the tubular body and extends into the conduit for securing the tubular body to the free end of the suture.

In one embodiment, the first end of the tubular body may form an interference fit or a compression fit with the attachment post of the needle.

In one embodiment, the first end of the tubular body may be swaged for securing the first end of the tubular body to the attachment post of the needle.

In one embodiment, the second end of the tubular body may be swaged for pinching the free end of the suture that extends into the conduit of the tubular body.

In one embodiment, the elongated body of the needle preferably includes a bore hole (e.g., a hole drilled in the elongated body of the needle) formed in a proximal end face at the proximal end of the elongated body. The hole may extend along a longitudinal axis of the needle.

In one embodiment, the first end of the connector preferably includes a wire inserted into the hole for securing the first end of the connector with the proximal end of the elongated body. In one embodiment, the second end of the connector preferably includes a tubular member having an opening that seats the free end of the suture for securing the connector to the free end of the suture.

In one embodiment, a needle and suture assembly may include a Nitinol needle having an elongated body including a proximal end and a distal end with a sharpened tip, a suture having a free end juxtaposed with the proximal end of the elongated body of the Nitinol needle, and a stainless steel connector disposed between the Nitinol needle and the suture.

In one embodiment, the stainless steel connector preferably includes a first end attached to the proximal end of the elongated body of the Nitinol needle and a second end attached to the free end of the suture. The Nitinol needle desirably has greater elasticity than the stainless steel connector, and the stainless steel connector desirably has greater plasticity than the Nitinol needle.

In one embodiment, the needle may include an attachment post projecting from the proximal end of the elongated body, whereby the elongated body of the needle has a first cross-sectional diameter and the attachment post of the needle has a second cross-sectional diameter that is smaller than the first cross-sectional diameter of the elongated body.

In one embodiment, the attachment post preferably includes a distal end secured to a proximal end face at the proximal end of the elongated body of the needle, the distal end of the attachment post having a first outer diameter, and a proximal end spaced from the distal end of the attachment post that defines a proximal-most end of the needle. In one embodiment, the proximal end of the attachment post desirably has a second outer diameter that is greater than the first outer diameter at the distal end of the attachment post. In one embodiment, the attachment post preferably has a lateral surface that extends along a length of the attachment post and that slopes inwardly between the proximal end and the distal end of the attachment post.

In one embodiment, the connector may include a tubular body having an elongated conduit that extends from a first opening at a first end of the tubular body to a second opening at a second end of the tubular body.

In one embodiment, the attachment post of the needle is preferably inserted into the first opening at the first end of the tubular body and extends into the elongated conduit for securing the first end of the tubular body with the attachment post of the needle.

In one embodiment, the free end of the suture is preferably inserted into the second opening at the second end of the tubular body and extends into the elongated conduit for securing the tubular body to the free end of the suture.

In one embodiment, the first end of the tubular body may include a first swage region that is deformable for securing the first end of the tubular body to the attachment post of the needle. In one embodiment, the second end of the tubular body may include a second swage region that is deformable for securing the second end of the tubular body to the free end of the suture.

In one embodiment, the first end of the tubular body desirably forms an interference fit or a compression fit with the attachment post of the needle.

In one embodiment, the elongated body of the needle may include a hole formed in a proximal end face at the proximal end of the elongated body. In one embodiment, the first end of the stainless steel connector desirably includes a wire that is adapted for insertion into the hole for securing the first end of the stainless steel connector with the proximal end of the elongated body. In one embodiment, the second end of the stainless steel connector preferably includes a tubular member having an opening that seats the free end of the suture for securing the stainless steel connector to the free end of the suture.

In one embodiment, the hole formed in the proximal end face of the elongated body desirably has an inner diameter of about 0.016 inches.

In one embodiment, the wire inserted into the hole preferably has an outer diameter of about 0.015 inches.

In one embodiment, the tubular member at the second end of the connector preferably has an inner diameter of about 0.020 inches and an outer diameter of about 0.028 inches.

In one embodiment, a needle and suture assembly preferably includes a curved surgical needle made of a superelastic alloy, the curved surgical needle including an elongated body having a proximal end and a distal end with a sharpened tip, and a suture having a free end juxtaposed with the proximal end of the elongated body of the curved surgical needle.

In one embodiment, the assembly preferably includes a connector disposed between the needle and the suture, the connector desirably having a first end attached to the proximal end of the elongated body of the curved surgical needle and a second end attached to the free end of the suture. In one embodiment, the connector may be made of a material having less elasticity and greater plasticity than the superelastic alloy of the curved surgical needle.

In one embodiment, the curved surgical needle desirably includes an attachment post projecting from a proximal end face at the proximal end of the elongated body, whereby the elongated body of the curved surgical needle has a first cross-sectional diameter and the attachment post has a second cross-sectional diameter that is smaller than the first cross-sectional diameter of the elongated body.

In one embodiment, the connector may include a tubular body having a conduit that extends from a first opening at a first end of the tubular body to a second opening at a second end of the tubular body.

In one embodiment, the attachment post of the needle is preferably inserted into the first opening at the first end of the tubular body and extends into the conduit for securing the first end of the tubular body with the attachment post of the curved surgical needle.

In one embodiment, the free end of the suture is preferably inserted into the second opening at the second end of the tubular body and extends into the conduit for securing the tubular body to the free end of the suture.

In one embodiment, the elongated body of the curved surgical needle may include a hole formed in a proximal end face of the elongated body.

In one embodiment, the first end of the connector may include a wire that is inserted into the hole for securing the first end of the connector with the proximal end of the elongated body, and the second end of the connector may include a tubular member having an opening that seats the free end of the suture for securing the connector to the free end of the suture.

In one embodiment, unique features may be imparted to the proximal end of the needle through processes such as vibratory milling without compromising other sections of the needle, such as the needle point.

In one embodiment, the attachment of a suture to a connector and the attachment of the connector to a needle may take place during two separate assembly stages.

It has been observed that drill life for drilling holes in Nitinol is much lower than drill life when drilling holes in stainless steel. In one embodiment, a needle has an attachment post used for coupling the needle with a suture so that severe processing challenges such as drill life when forming suture receiving bores in Nitinol needles may be eliminated since no hole drilling is necessary.

In one embodiment, the metallic, tubular-shaped connector couples an end of a suture with the proximal end of the needle such as by forming a mechanically fit over both the needle and the suture. In one embodiment, the connector is preferably made of stainless steel such as austenitic stainless steel. In one embodiment, the austenitic stainless steel may be 316 stainless steel (316SS). In one embodiment, the austenitic stainless steel may be annealed. In one embodiment, the austenitic stainless steel may be "half-hard." In one embodiment, the austenitic stainless steel may be "fully-hard."

In one embodiment, the connector preferably exhibits substantial strength to avoid excessive deformation and damage to the suture as the needle inserted or removed from the trocar.

In one embodiment, the connector does not plastically deform under the mechanical spring pressure generated by the superelastic needle as it traverses the trocar, thereby protecting the suture attachment site from damage.

In one embodiment, the attachment post has a round or circular cross-sectional dimension. In one embodiment, the outer diameter of the attachment post tapers inwardly at an angle of about one degree or greater to preferably enhance the strength of the mechanical attachment between the connector and the needle. In one embodiment, the distal end of the attachment post may be flared and/or have an annular flange that extends outwardly at the distal end of the attachment post.

In one embodiment, the connector attachment to the needle or the suture may be achieved by swaging (e.g., stakes, square dies, round dies, flat dies, and/or combinations thereof with one or more swaging strikes).

In one embodiment, connector attachment may be achieved by an interference fit. In one embodiment, the connector attachment may be achieved by longitudinal compression fit. In one embodiment, the connector attachment may be achieved by using an adhesive, or through any combination of the aforementioned methodologies.

In one embodiment, the systems, devices and methods disclosed herein may be applied to the distal end of the needle (i.e., the end having a sharpened tip) should a need arise to make a needle having a needle point that is made of a material other than Nitinol.

In one embodiment, the connector may include a body having a smaller diameter first section (e.g., a section having the configuration of a wire) and a larger diameter second section having a tubular shape. In one embodiment, the connector may be formed by obtaining a tubular shaped body, such as a body made of stainless steel, and swaging (e.g., rotary swaging) the first section of the connector into a component having a diameter and shaped of a wire.

In one embodiment, the smaller diameter first section of the connector is preferably adapted to be inserted into hole (e.g., a drilled hole) formed in an end of the needle. In one embodiment, the attachment of the connector to the needle is generated by providing friction between the inside of the hole in the needle metal and the first section of the connector. In one embodiment, the hole or the outer surface of the first section of the connector may be serrated or adapted to generate high levels of friction to provide an interlocking mechanism of the first section of the connector with the inside of the hole.

In one embodiment, the material used for the connector has higher strength than the suture material, and a higher plasticity than the needle material.

In one embodiment, the first end of the connector may have a much smaller diameter than the diameter of the suture since the tensile strength is higher between the needle hole and the first section of the connector is much higher.

In one embodiment, the length or depth of the hole formed in the needle may be relatively short because the frictional force and interlocking features require less surface contact than would be needed for forming an attachment with a polymer suture.

In one embodiment, the length of the first section of the connector may be equal to or less than the length or depth of the needle hole.

In one embodiment, the smaller diameter first end of the connector may be made from rotary swaging a tube, which provides higher strength material through cold working of a soft material.

In one embodiment, the larger diameter second section of the connector may have an opening at an end thereof having a diameter that can be obtained from an initial tube material providing for an accurate diameter and consistency for the second section of the connector.

In one embodiment, the second section of the connector is designed for receiving an end of a suture to provide for a longer surface contact region between the connector and the suture for swaging and a plastic material to conform to the suture without over-compression of the suture that may damage the suture.

In one embodiment, the length of the second section of the connector is not limited to the features of the needle features so that the pull force of the suture is proportional to the length of the swaging zone between the connector and the suture (e.g., up to the tensile strength of the suture).

In one embodiment, the tube shaped opening at the second section of the connector may include a tapered edge or surface to avoid and/or minimize damage to the suture as it is inserted into the second section of the connector and swaged.

In one embodiment, the connector disclosed herein provides a universal adapter for securing sutures to needles because the diameter and length of the second section of the connector is independent of and not determined by the size, length, and/or depth of the hole formed in the needle.

In one embodiment, connectors may be color coded for indentifying different types and sizes of sutures.

In one embodiment, a connector may provide plastic deformation to follow the curvature of a needle.

In one embodiment, a connector may be made of a magnetic material to allow easy transportation during needle manufacturing.

In one embodiment, a connector is made using 304 stainless steel hypodermic needle tubing. In one embodiment, the tubing has an inner diameter of 0.020 inches and an outer diameter of 0.028 inches. In one embodiment, rotary swaging may be used to reduce the diameter of the first section of the connector to 0.015 inches. In one embodiment, a needle made of a super elastic material has a hole formed therein having an inner diameter of 0.016 inches and a needle hole depth of about 0.060 inches.

In one embodiment, both the suture and the needle may be swaged to the connector using a square swage technique adapted to the diameter of the needle and the second section of the connector.

In one embodiment, the strength of the attachment between the needle and the connector exceeded the capacity of a load cell (i.e., seven kilograms) and did not break at the capacity level.

In one embodiment, the strength of the attachment between the connector and the suture exceeded five kilograms (5 KG)

In one embodiment, the length of the connector may be reduced to the length of the suture swage region and taper down length of the first section of the connector.

In one embodiment, the strength of the needle attachment is proportional to the length of the suture swage and may be tailored to the needs of a surgeon, and may be balanced with the acceptable length of the swage for other surgical requirements.

These and other preferred embodiments of the present invention will be described in more detail below.

BRIEF DESCRIPTION OF THE DRAWINGS

FIG. 9D shows a fourth step of a method of using the connector of FIGS. 8A-8B for coupling a suture with a surgical needle, in accordance with one embodiment of the present patent application.

FIG. 9E shows a fifth step of a method of using the connector of FIGS. 8A-8B for coupling a suture with a surgical needle, in accordance with one embodiment of the present patent application.

FIG. 13B shows a second step of a method of using a tubular connector for securing a suture to a curved surgical needle, in accordance with one embodiment of the present patent application.

FIG. 14B shows a second step of a method of using a tubular connector for securing a suture to a curved surgical needle, in accordance with one embodiment of the present patent application.

DETAILED DESCRIPTION OF PREFERRED EMBODIMENTS

Figure 1:
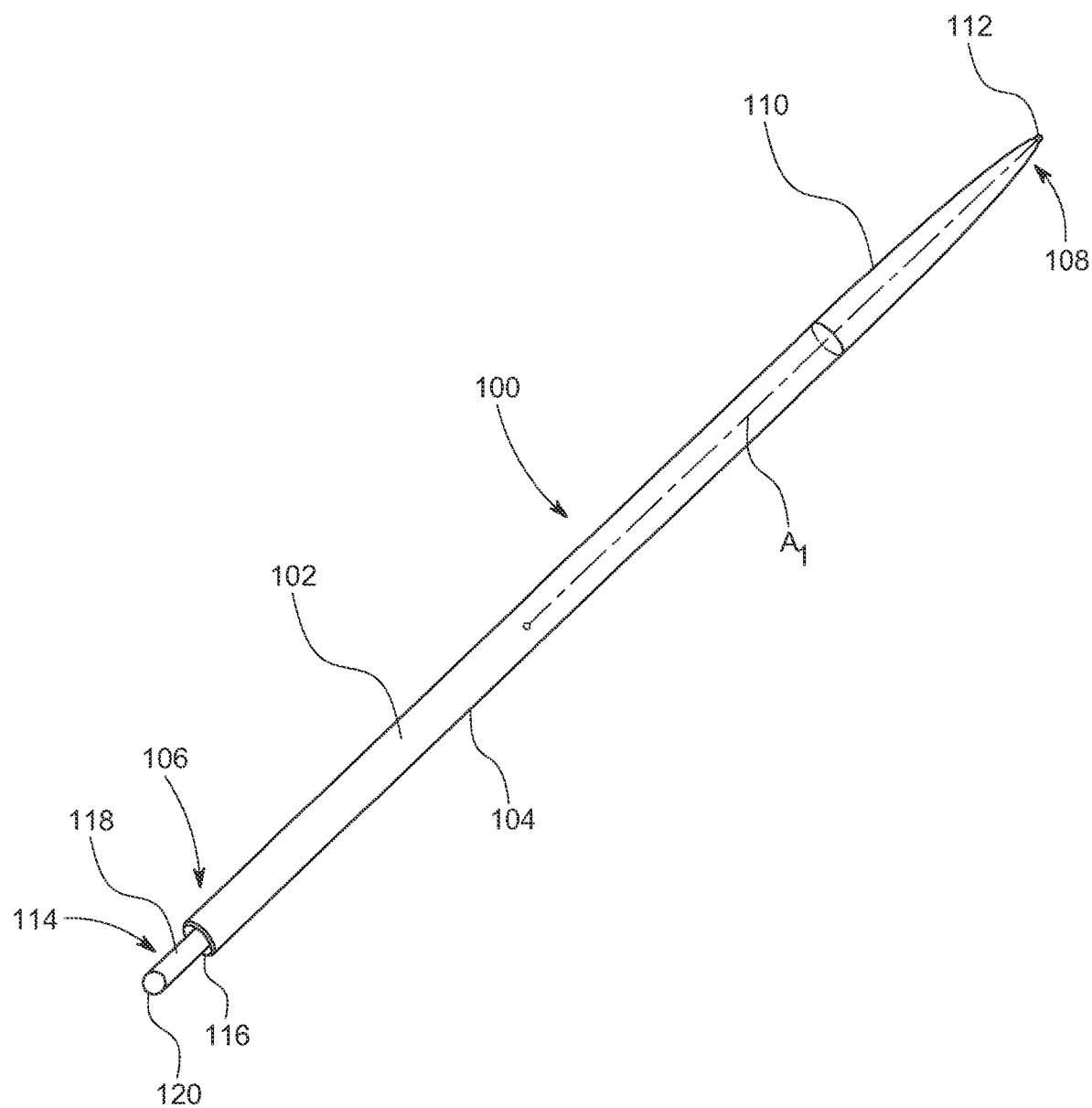
FIG. 1 is a perspective view of a needle having an attachment post projecting from a proximal end thereof, in accordance with one embodiment of the present patent application.

Referring to FIG. 1, in one embodiment, a needle 100, such as a surgical needle or a suture needle, preferably has an elongated body 102 with an outer surface 104 that extends along the length of the needle. In one embodiment, the needle 100 preferably has a proximal end 106, a distal end 108, and a longitudinal axis $A_1$ that extends along the length of the needle from the proximal end 106 to the distal end 108 thereof. In one embodiment, the elongated body 102 of the needle 100 has a generally cylindrical shape with a circular cross-section. In one embodiment, the distal end 108 of the needle 100 desirably has a tapered region 110 that terminates at a sharpened tip 112, which is located at a distal-most end of the needle 100.

The needle may be made of a superelastic alloy such as Nitinol that provides exceptional elastic recovery properties to the needle. In one embodiment, the needle may be a curved suture needle as disclosed in FIGS. 13A-13B and 14A-14B of the present patent application. The curved suture needle may be designed to flatten or straighten for passing through a smaller diameter tube, cannula, or trocar (e.g., a 5 mm trocar).

In one embodiment, the needle 100 desirably includes an attachment post 114 that preferably projects proximally from the proximal end 106 of the elongated body 102 of the needle 100. In one embodiment, the attachment post 114 projects proximally from a proximal end face 116 of the elongated body 102, which is located at the proximal end 106 of the needle 100. In one embodiment, the attachment post 114 preferably includes a distal end 118 that is connected to the proximal end face 116, and a proximal end 120, spaced from the distal end of the attachment post, which defines a proximal-most end of the needle 100.

In one embodiment, the attachment post 114 may be formed by removing material from the outer surface 104 of the elongated body 102 of the needle 100 so that the attachment post 114 has a smaller outer diameter than the outer diameter of the elongated body 102 of the needle 100. In one embodiment, the material is removed for forming the attachment post using milling or grinding equipment. In one embodiment, the attachment post may be formed by connecting a pre-formed post to the proximal end face 116 of the needle 100.

Figure 2:
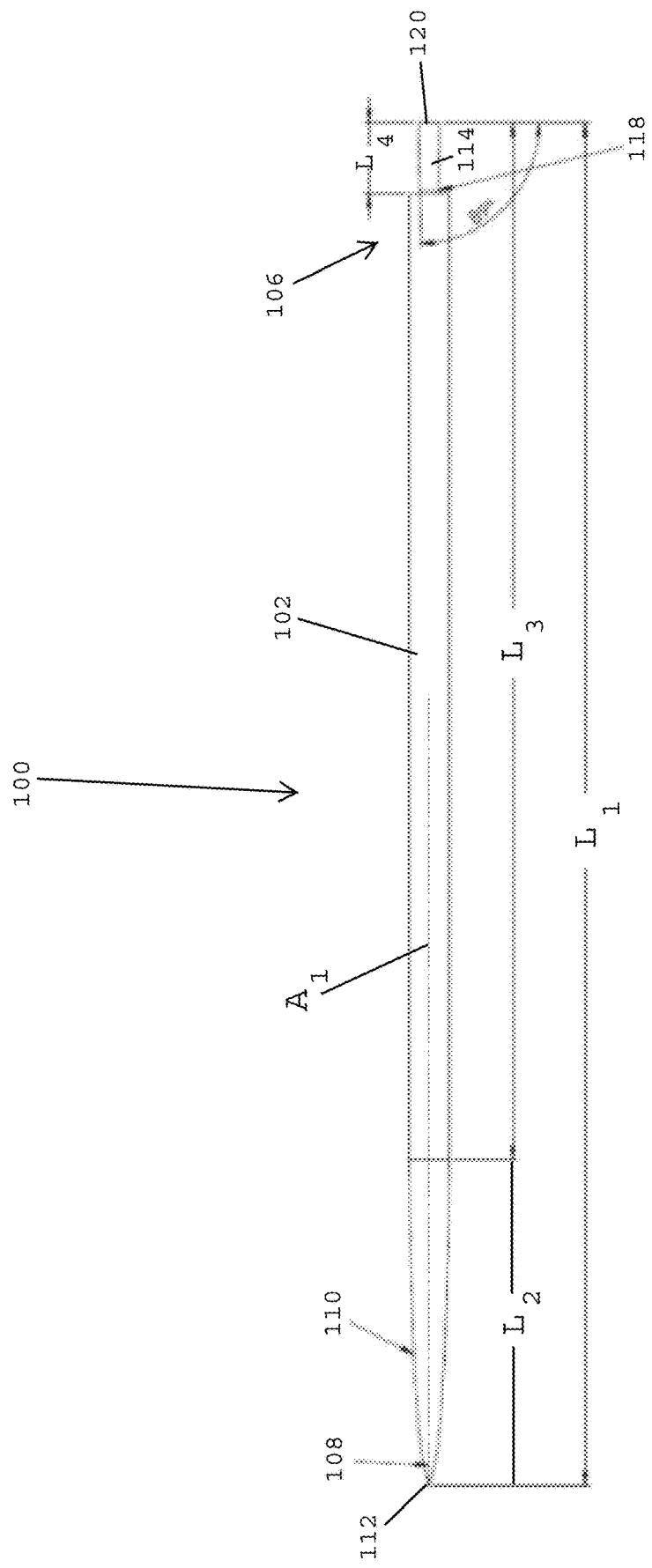
FIG. 2 is a side view of the needle shown in FIG. 1.

Referring to FIG. 2, in one embodiment, the needle 100 preferably has the elongated body 102 that extends along the axis $A_1$ between the proximal end 106 and the distal end 108 of the needle 100. The needle 100 desirably includes the tapered region 110 that terminates at a sharpened tip 112, which defines the distal-most end of the needle 100. The attachment post 114 preferably projects from the proximal end face 116 (FIG. 1) located at the proximal end 106 of the elongated body 102 of the needle. The attachment post 114 preferably has a distal end 118 secured to the proximal end face 116 of the elongated body 102 and a proximal end 120 that defines a proximal-most end of the needle 100.

In one embodiment, the needle 100 has a length $L_1$ of about 1.0-3.0 inches, more preferably about 1.0-2.0 inches, and even more preferably about 1.34 inches, which extends from the proximal end 120 of the attachment post 114 to the sharpened tip 112 at that distal-most end of the needle 100. In one embodiment, the tapered region 110 of the needle has a length $L_2$ of about 0.25-0.50 inches, and more preferably about 0.32 inches. In one embodiment, a length $L_3$ of the needle 100 minus the tapered region 110 is about 0.75-1.25 inches, and more preferably about 1.02 inches. In one embodiment, the attachment post 114 has a length $L_4$ of about 0.050-0.100 inches, and more preferably about 0.070 inches.

Figure 3A:
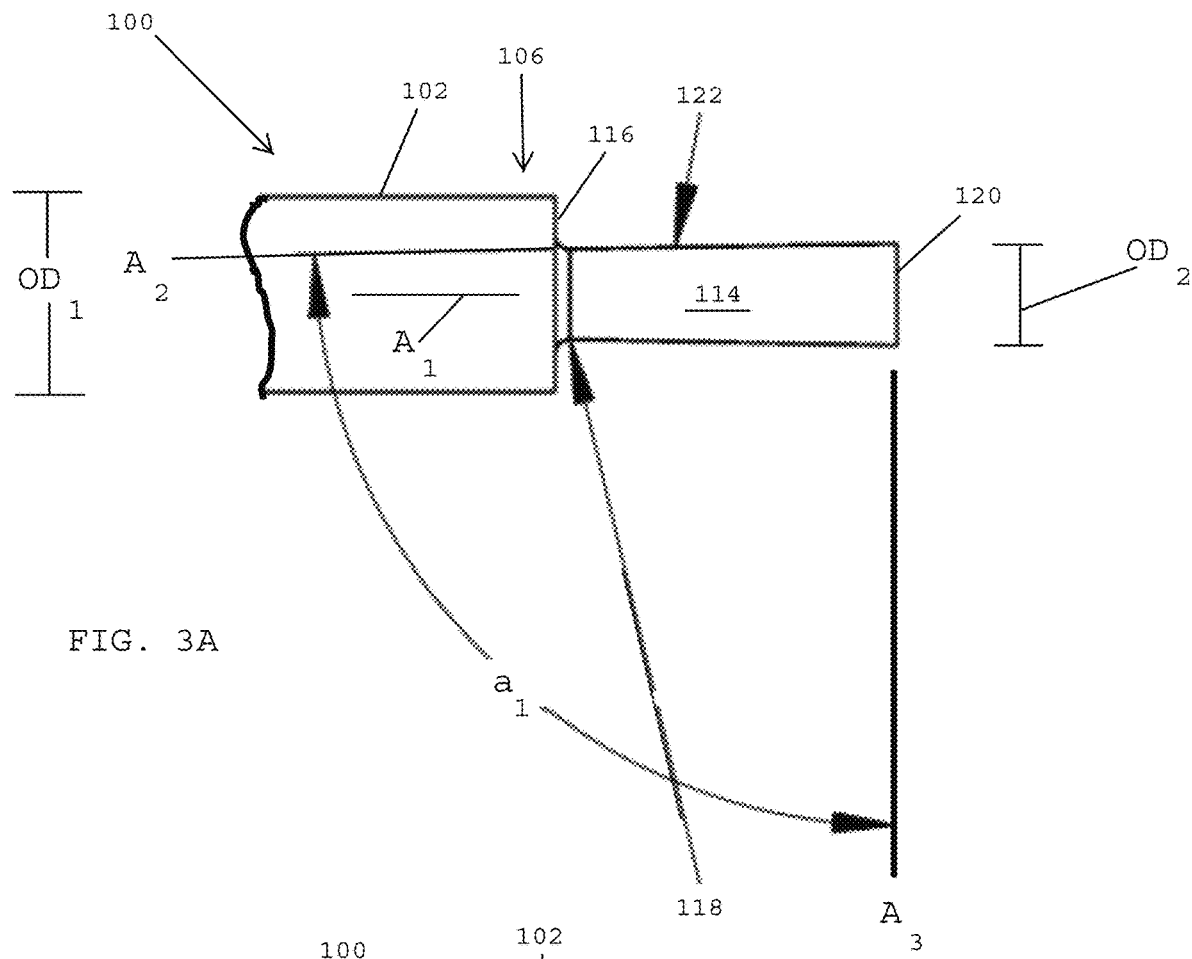
FIG. 3A is a magnified view of the attachment post projecting from the proximal end of the needle shown in FIGS. 1 and 2.
Figure 3B:
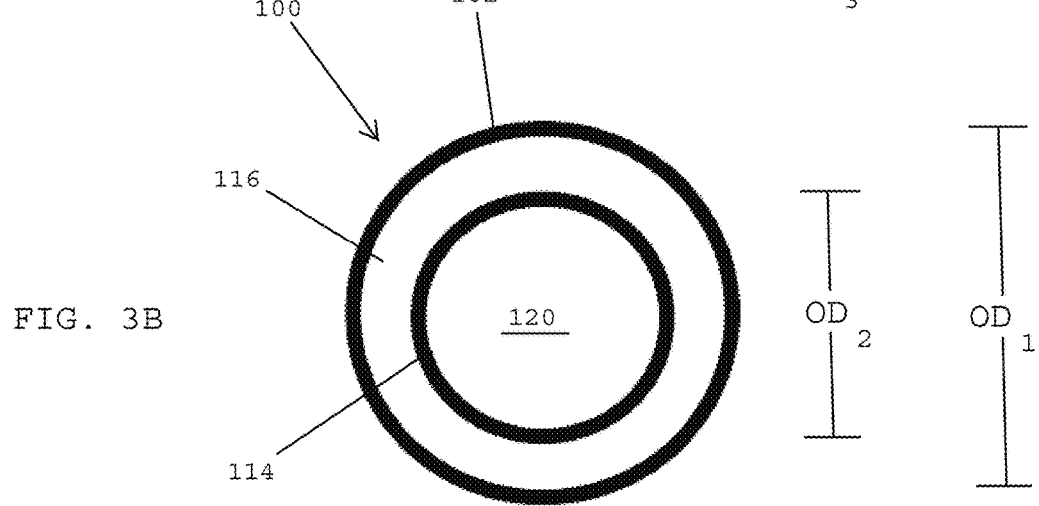
FIG. 3B is a cross-sectional view of the needle including the attachment post shown in FIG. 3A.

Referring to FIGS. 3A and 3B, in one embodiment, the attachment post 114 preferably projects from the proximal end face 116 located at the proximal end 106 of the elongated body 102 of the needle 100. The attachment post 114 desirably extends along the longitudinal axis $A_1$ of the needle 100.

In one embodiment, the attachment post 114 preferably has the distal end 118 secured to the proximal end face 116 of the elongated body 102 and the proximal end 120, spaced from the distal end 118, that defines the proximal-most end of the needle 100. The attachment post 114 has a lateral surface 122 extending between the proximal and distal ends of the attachment post that tapers inwardly between the proximal end 120 and the distal end 118 thereof. In one embodiment, the tapered surface 102 tapers inwardly along an axis $A_2$ that defines an angle $\alpha_1$ of about 89° with an axis $A_3$ that is perpendicular to the longitudinal axis $A_1$ of the needle 100. Stated alternatively, the tapered surface tapers inwardly at an angle of about one degree (1°) relative to the longitudinal axis of the needle 100.

In one embodiment, the elongated body 102 of the needle 100 has a larger outer diameter than the outer diameter of the attachment post 114 of the needle. In one embodiment, the elongated body 102 of the needle 100 defines an outer diameter $OD_1$ of about 0.040 inches. In one embodiment, the attachment post 114 of the needle 100 defines an outer diameter $OD_2$ of about 0.021 inches.

Figure 4A:
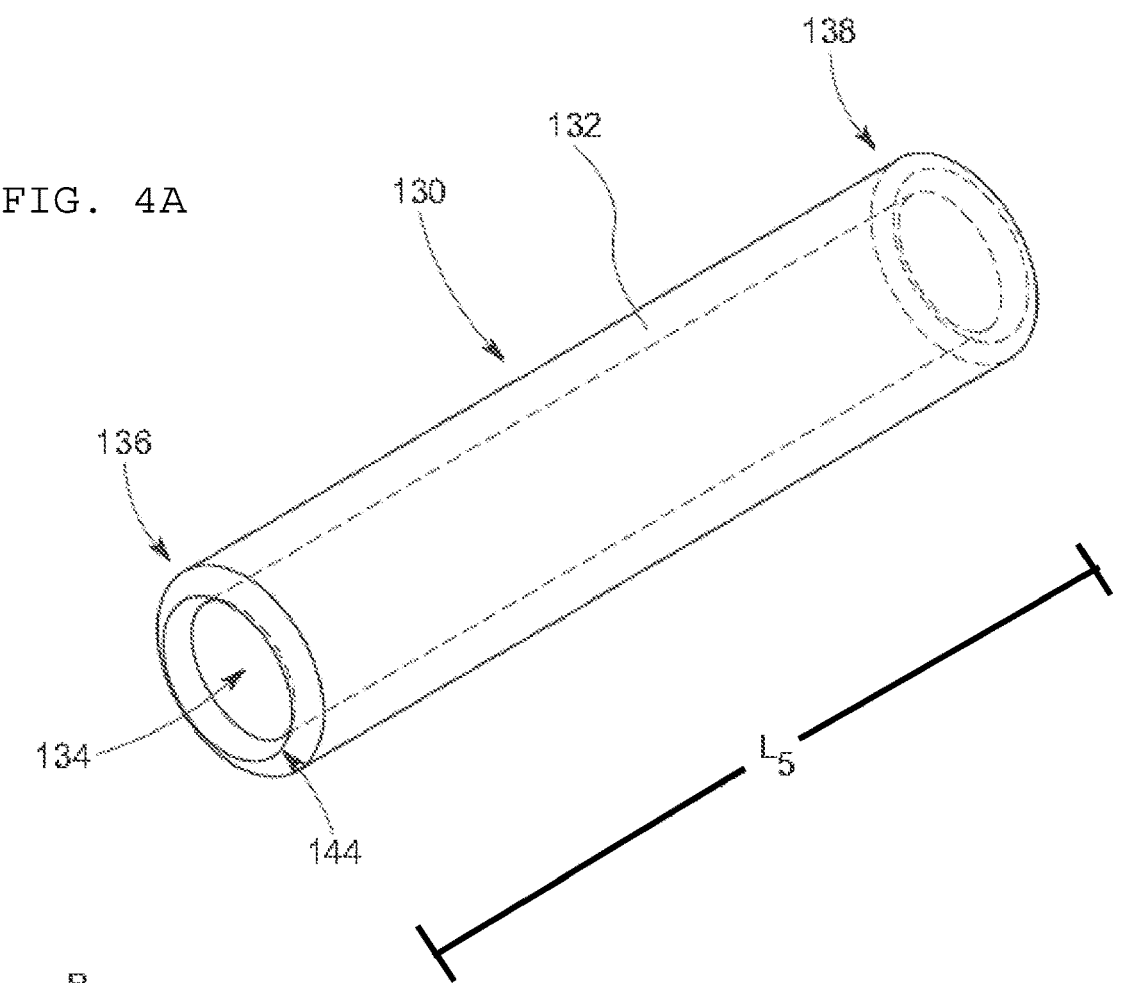
FIG. 4A is a perspective view of a connector used for securing a suture to the needle shown in FIGS. 1 and 2, in accordance with one embodiment of the present patent application.
Figure 4B:
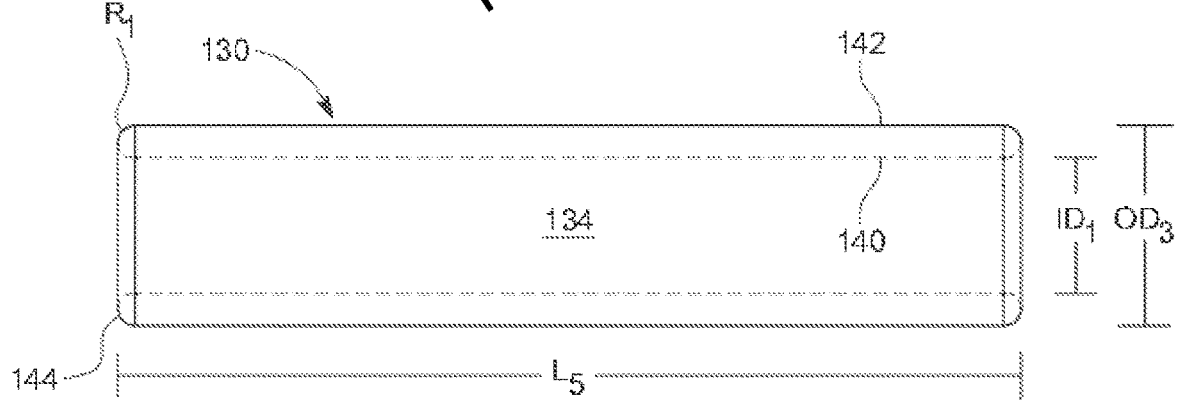
FIG. 4B is a front elevation view of the connector shown in FIG. 4A.
Figure 4C:
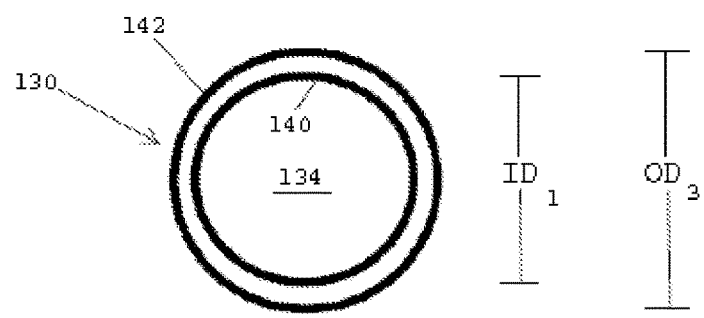
FIG. 4C is a cross-sectional view of the connector shown in FIGS. 4A and 4B.

Referring to FIGS. 4A-4C, in one embodiment, a connector 130 may be utilized for securing a suture to the proximal end of the needle shown and described above in FIGS. 1-3B. The connector 130 may be made of a material that has less elasticity and more plasticity than the needle shown and described above in FIGS. 1-3B. In one embodiment, the needle is made of a superelastic alloy such as Nitinol and the connector is made of stainless steel. In one embodiment, the connector 130 preferably includes a tubular body 132 having an elongated conduit 134 that extends from a first end 136 to a second end 138 of the connector. In one embodiment, the tubular body 132 desirably has an inner surface 140 that surrounds and defines the conduit 134 of the connector 130, and an outer surface 142 that defines an outer diameter of the connector 130.

Referring to FIG. 4B, in one embodiment, the connector 130 has a length $L_5$ of about 0.100-0.200 inches, and more preferably about 0.160 inches. In one embodiment, the first and second ends 136, 138 of the tubular body 132 may be rounded, such as via vibratory milling, to provide rounded ends for the connector 130. In one embodiment, a rounded end 144 preferably defines a radial surface $R_1$ having a radius of about 0.003 inches.

Referring to FIGS. 4B and 4C, in one embodiment, the outer surface 142 of the tubular body 132 of the connector 130 preferably defines an outer diameter $OD_3$ of about 0.0355 inches. In one embodiment, the inner surface 140 of the tubular body 132 preferably defines an inner diameter $ID_1$ of about 0.0235 inches. The inner diameter of the connector is preferably sized so that the tubular body may be secured over the outer diameter of the attachment post 114 (FIG. 1) that projects from the proximal end face of the needle.

Referring to 5A, in one embodiment, the connector 130 shown and described above in FIGS. 4A-4C may be utilized for connecting a suture 150 with the needle 100 described above in FIGS. 1-3B. In one embodiment, the connector 130 desirably includes the tubular body 132 having a tubular shape with a first end 136 and a second end 138. The elongated conduit 134 of the connector desirably extends along the length of the connector 130 and provides openings at the respective first and second ends 136, 138 of the tubular body.

Figure 5A:
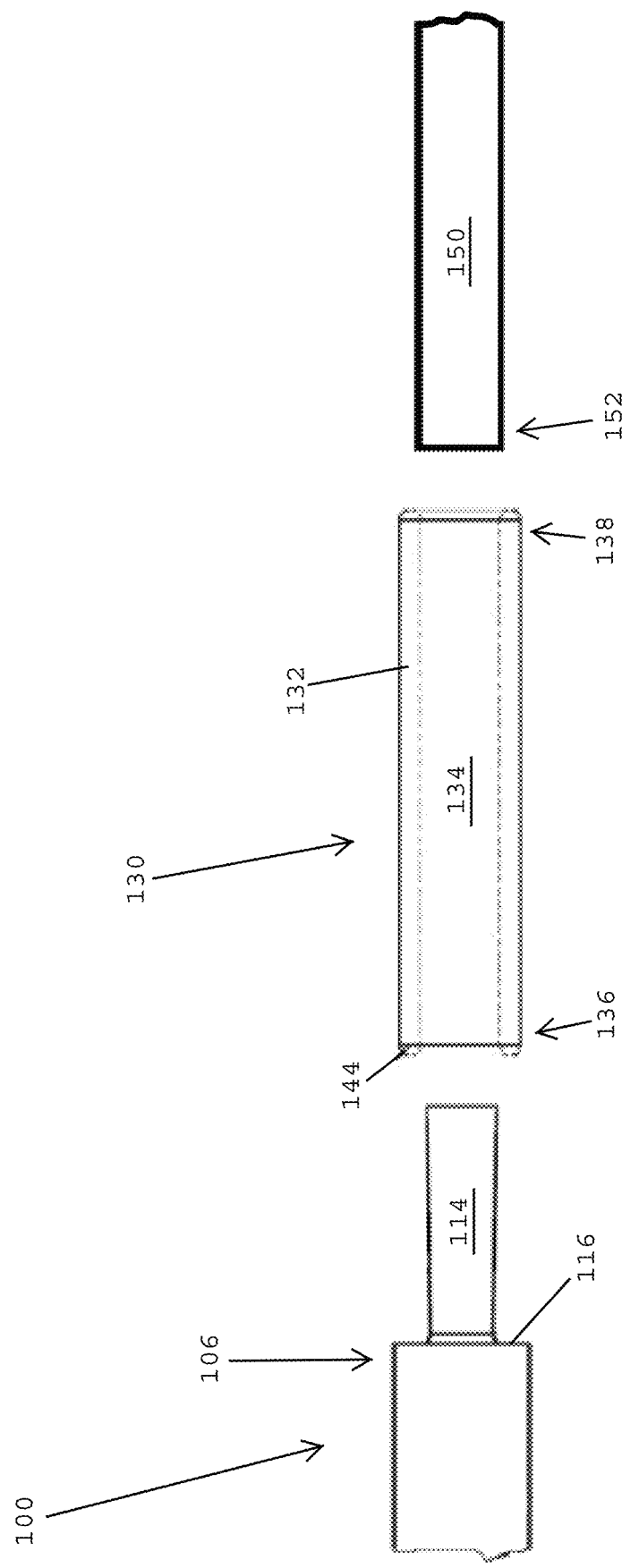
FIG. 5A shows a first step of a method of using the connector of FIGS. 4A-4C to secure a suture to a needle, in accordance with one embodiment of the present patent application.
Figure 5B:
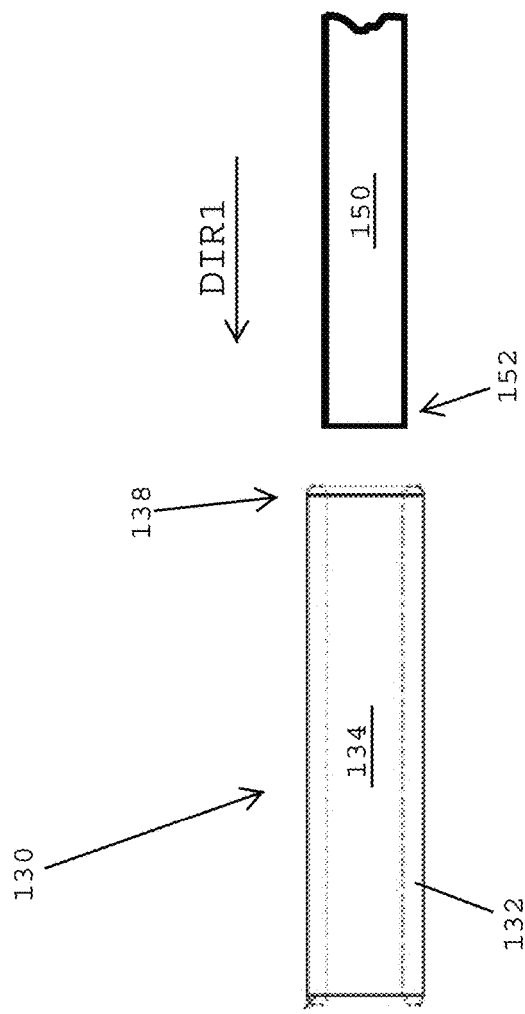
FIG. 5B shows a second step of a method of using the connector of FIGS. 4A-4C to secure a suture to a needle, in accordance with one embodiment of the present patent application.
Figure 5C:
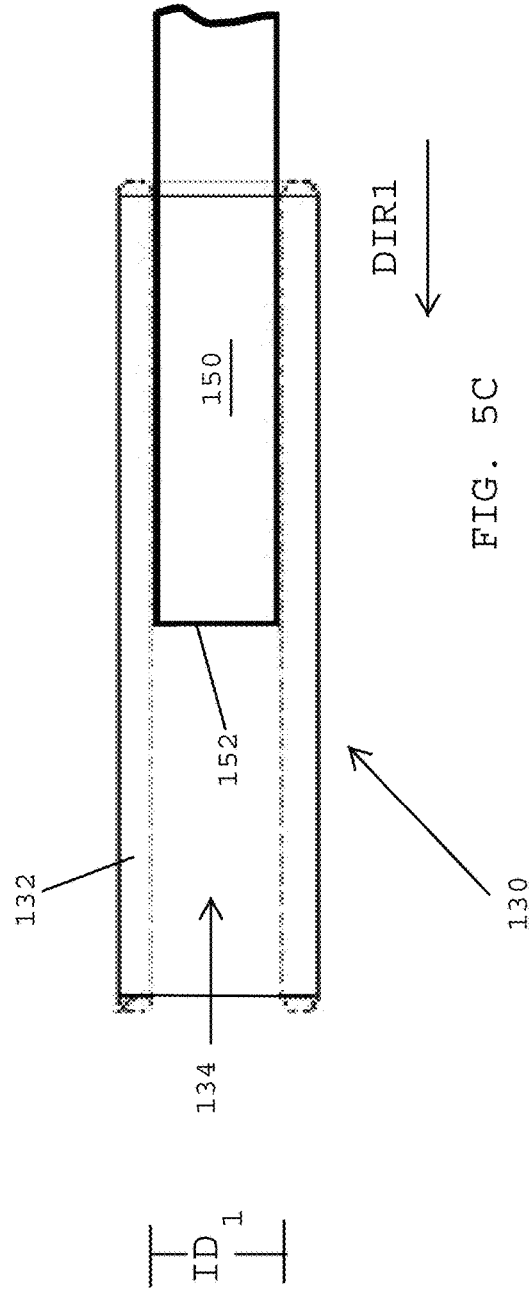
FIG. 5C shows a third step of a method of using the connector of FIGS. 4A-4C to secure a suture to a needle, in accordance with one embodiment of the present patent application.

Referring to FIG. 5B, in one embodiment, a distal end 152 of the suture 150 is desirably positioned adjacent the second end 138 of the tubular body 132 of the connector. Referring to FIGS. 5B and 5C, the distal end 152 of the suture 150 is preferably aligned with the opening located at the second end 138 of the tubular member 132, which is aligned with the elongated conduit 134. In one embodiment, the suture is desirably advanced in the direction designated DIR1 so that the distal end 152 of the suture 150 is positioned within the conduit 134 of the tubular body 132. In one embodiment, the suture may have an outer diameter that closely matches the inner diameter $ID_1$ of the tubular body 132 of the connector 130.

Referring to FIG. 5C, in one embodiment, after the distal end 152 of the suture 150 is positioned inside the tubular body 132 of the connector 130, the outer surface 142 of the tubular body 132 may be swaged or crimped for deforming a swaged region SR of the tubular body 132 to secure the connector 130 to the distal end 152 of the suture 150. The region of the connector 130 that surrounds the suture 150 is desirably swaged for forming a secure connection between the suture 150 and the connector 130. In one embodiment, after swaging, the swaged region SR of the tubular body may be deformed inwardly relative to the first end 136 of the tubular body 132 so that the swaged region SR has a smaller outer diameter than the first end 136 (i.e., the unswaged region) of the tubular body.

Figure 5D:
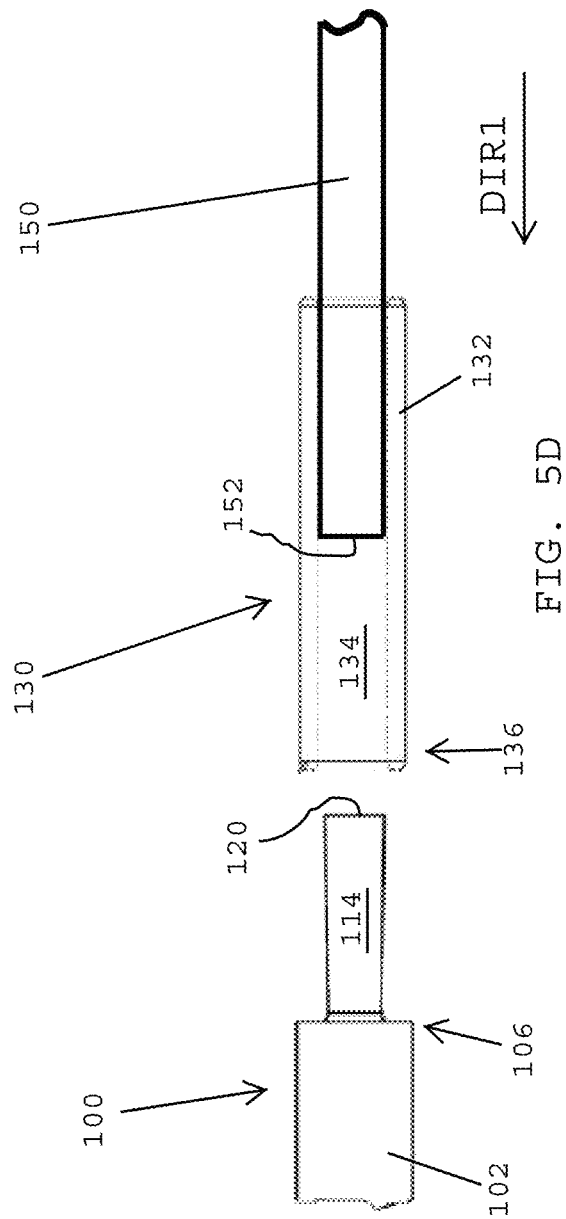
FIG. 5D shows a fourth step of a method of using the connector of FIGS. 4A-4C to secure a suture to a needle, in accordance with one embodiment of the present patent application.
Figure 5E:
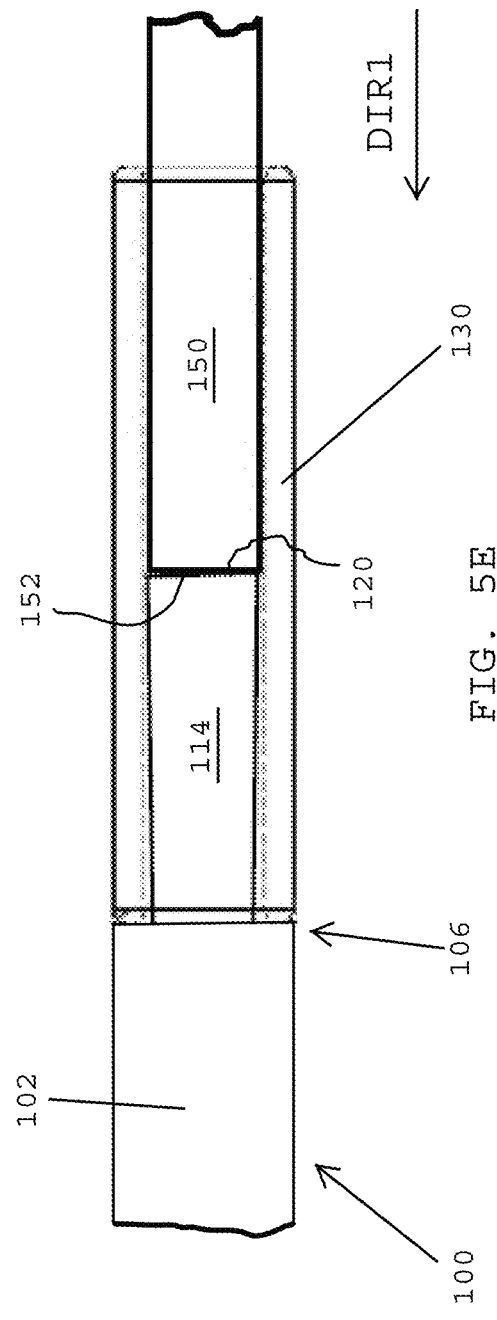
FIG. 5E shows a fifth step of a method of using the connector of FIGS. 4A-4C to secure a suture to a needle, in accordance with one embodiment of the present patent application.

Referring to FIG. 5D, in one embodiment, after the connector 130 has been secured to an end of the suture 150, the attachment post 114 projecting from the proximal end 106 of the needle 100 may be aligned with the elongated conduit 134 at the first end 136 of the tubular body 132 of the connector 130. Referring to FIGS. 5D and 5E, the connector 130 is preferably advanced over the attachment post 114 of the needle 100 in the direction designated DIR1 until the rounded edge 144 at the first end 136 of the tubular body 132 abuts against the proximal end face 116 located at the proximal end 106 of the elongated body 102 of the needle 100. In one embodiment, the distal end 120 of the attachment post 114, disposed within the tubular body 132 of the connector 130, may abut against the distal end 152 of the suture 150.

In one embodiment, it may be preferable to first secure the connector to the attachment post of the suture needle followed by securing the connector to the end of the suture. In one embodiment, the connector 130 is preferably first attached to the attachment post 114 using a first mechanical swaging operation, and subsequently, the suture 150 may be connected to the connector 130 in a second mechanical swaging operation that follows the first mechanical swaging operation.

Figure 6:
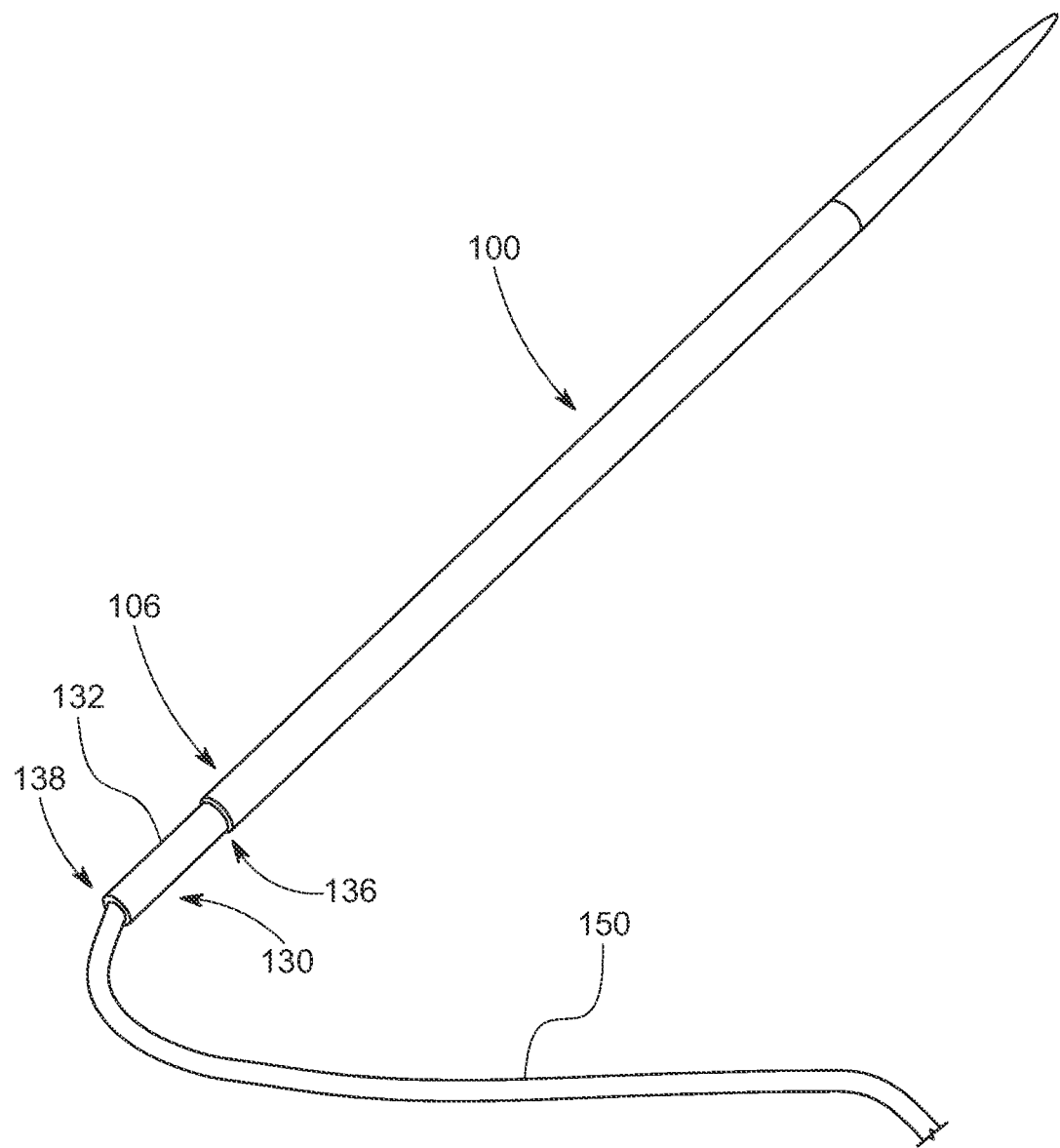
FIG. 6 shows a perspective view of a surgical needle and a suture that are coupled together using a connector, in accordance with one embodiment of the present patent application.

FIG. 6 shows the suture 150 (FIG. 5E) after it has been secured to the needle 100. The connector 130 preferably includes the tubular body 132 having the first end 136 secured to the attachment post 114 (FIG. 1) that projects proximally from the proximal end 106 of the needle 100 and the second end 138 swaged for being secured to the distal end of the suture 150. In one embodiment, the needle 100 is preferably made of a material that is more elastic than the connector 130. In one embodiment, the connector 130 is made of a material that exhibits more plasticity than the material used to make the needle 100. In one embodiment, the needle 100 is preferably curved as disclosed in the embodiments shown in FIGS. 13A-13B and 14A-14B of the present patent application.

Figure 7A:
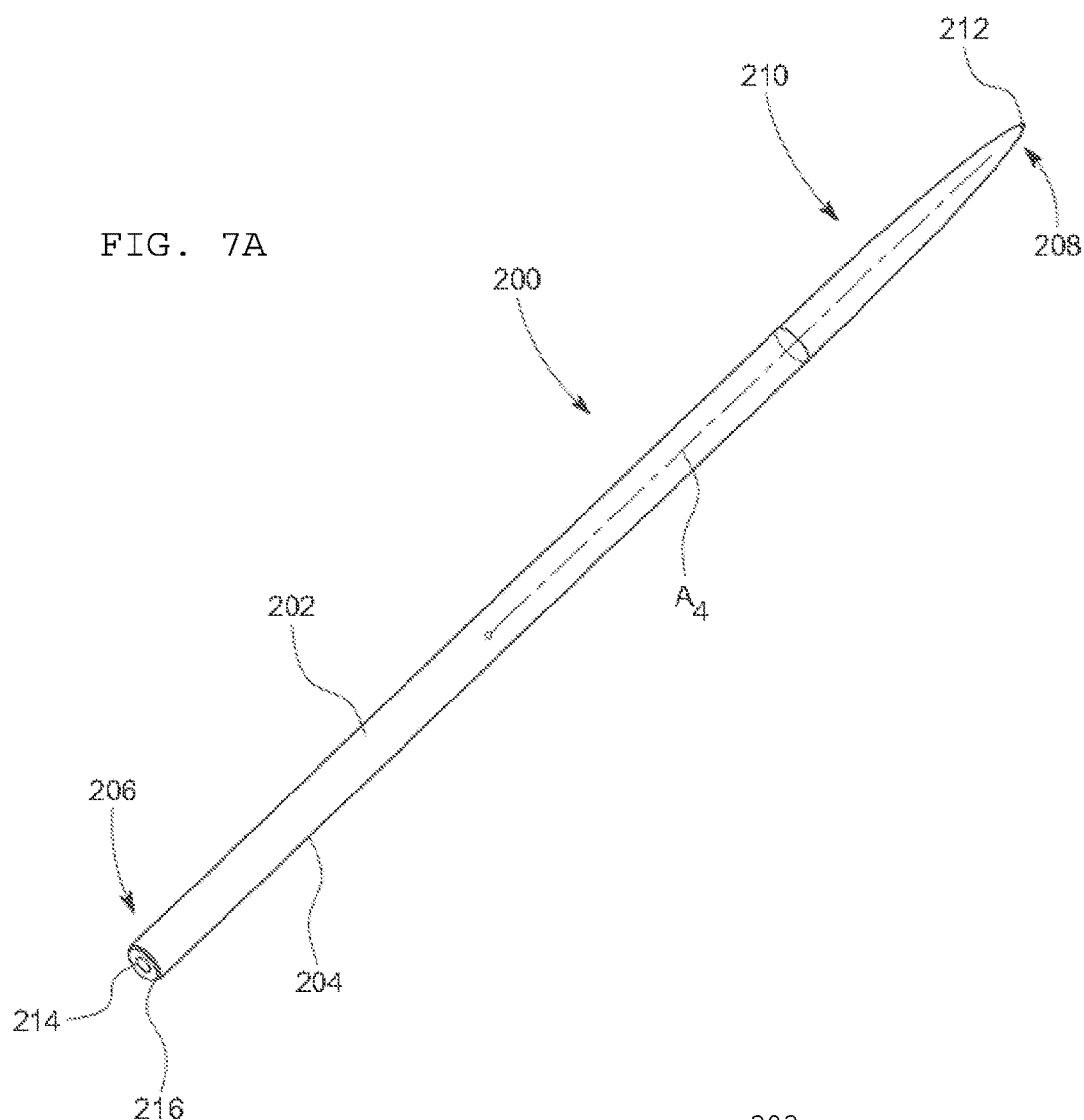
FIG. 7A is a perspective view of a needle having a hole drilled in a proximal end face, in accordance with one embodiment of the present patent application.

Referring to FIG. 7A, in one embodiment, a needle 200 preferably includes an elongated body 202 having an outer surface 204 that extends along the length of the needle. The needle 200 may be made of a superelastic alloy having shape memory properties. The needle 200 preferably has a proximal end 206, a distal end 208 and an elongated axis $A_4$ that extends along the length of the needle from the proximal end 206 to the distal end 208 thereof. The needle 200 preferably includes a tapered region 210, at the distal end 210 of the needle, which terminates at a sharpened tip 212 that defines a distal-most end of the needle. In one embodiment, the needle 200 preferably includes a hole 214 (e.g., a drilled hole or opening) that is desirably formed in a proximal end face 216 of the elongated body 202. In one embodiment, the hole 214 is co-axial with the longitudinal axis $A_4$ of the needle 200. In one embodiment, the needle 200 may be curved as shown in FIGS. 13A-13B and 14A-14B of the present patent application.

Figure 7B:
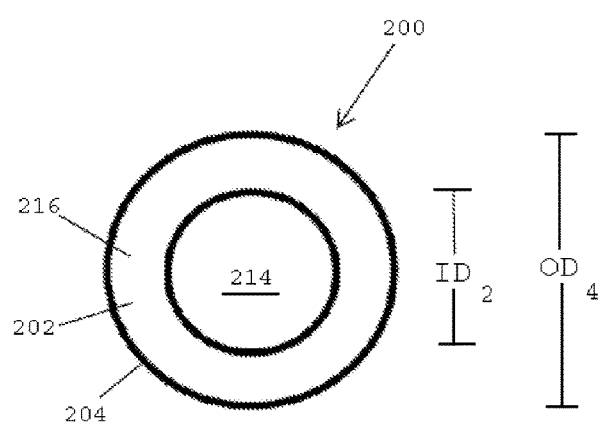
FIG. 7B is a proximal end view of the needle shown in FIG. 7A.

Referring to FIG. 7B, in one embodiment, the hole 214 formed in the proximal end face 216 of the needle preferably defines an inner diameter $ID_2$ of about 0.016 inches. In one embodiment, the outer surface 204 of the elongated body 202 of the needle 200 defines an outer diameter $OD_4$ of about 0.040 inches.

Figure 7C:
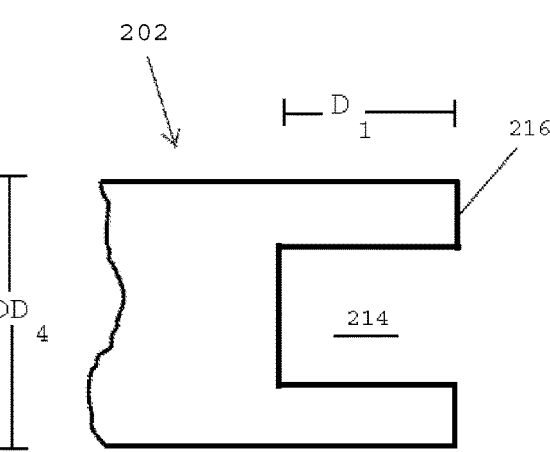
FIG. 7C is a cross-sectional view of the proximal end of the needle shown in FIGS. 7A and 7B.

Referring to FIG. 7C, in one embodiment, the hole 214 formed in the proximal end face 216 of the needle 200 desirably has a depth $D_1$ of about 0.050-0.075 inches, and more preferably about 0.060 inches.

Figure 8A:
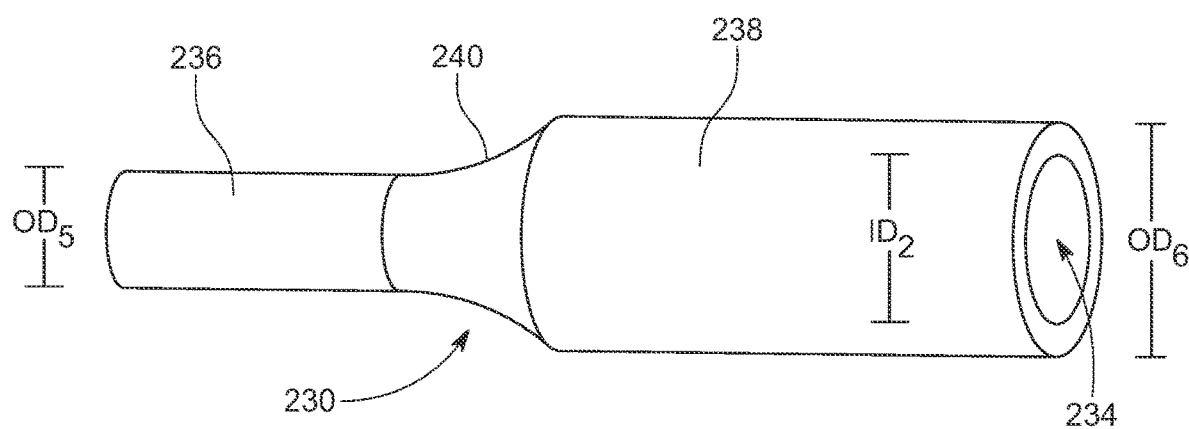
FIG. 8A is a side view of a connector used to couple a suture with a surgical needle, in accordance with one embodiment of the present patent application.
Figure 8B:
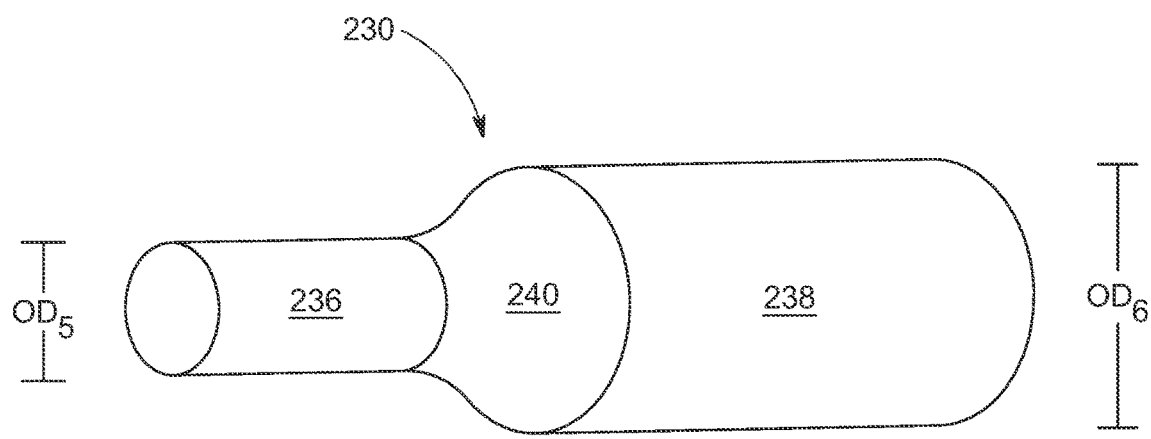
FIG. 8B is a perspective view of the connector shown in FIG. 8A.

Referring to FIGS. 8A and 8B, in one embodiment, a connector 230 used for coupling a suture with a surgical needle preferably has a first section 236 that defines a smaller diameter region of the connector and a second section 238 that defines a larger diameter region of the connector. In one embodiment, the outer surface of the connector 230 preferably has a sloping surface 240 that extends from the smaller diameter first section 236 to the larger diameter second section 238.

In one embodiment, the larger diameter second section 238 of the connector 230 preferably has a tubular shaped body with an opening 234 that extends along the length of the second section 238. In one embodiment, the connector 230 may be made by first obtaining a tubular structure. In one embodiment, the first section 136 of the tubular structure is desirably crimped, swaged, and/or compressed to form the smaller diameter first section 236, which has an outer diameter that is smaller than the outer diameter of the second section 238 that includes the opening 234. In one embodiment, the first section 236 of the connector 230 preferably defines an outer diameter $OD_5$ of about 0.015 inches. In one embodiment, the first section 236 of the connector 230 may have the shape and configuration of a wire. In one embodiment, the second section 238 of the connector 230 having the opening 234 preferably defines an outer diameter $OD_6$ of about 0.028 inches and an inner diameter $ID_2$ of about 0.020 inches. The opening 234 within the second section 238 of the connector 230 is preferably adapted to receive an end of a suture for securing the connector 230 to the end of the suture.

Figure 9A:
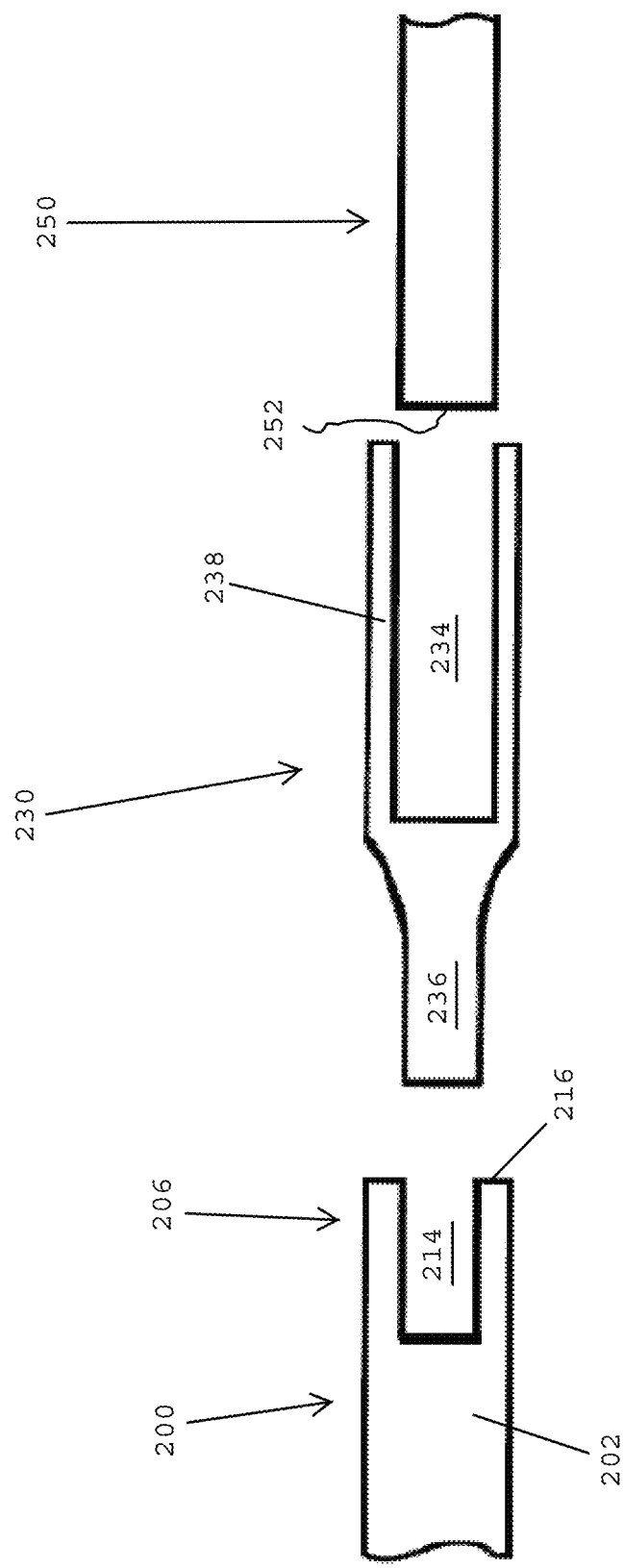
FIG. 9A shows a first step of a method of using the connector of FIGS. 8A-8B for coupling a suture with a surgical needle, in accordance with one embodiment of the present patent application.

Referring to FIG. 9A, in one embodiment, the connector 230 may be utilized for securing a distal end 252 of a suture 250 to the proximal end 206 of the needle 200.

Figure 9B:
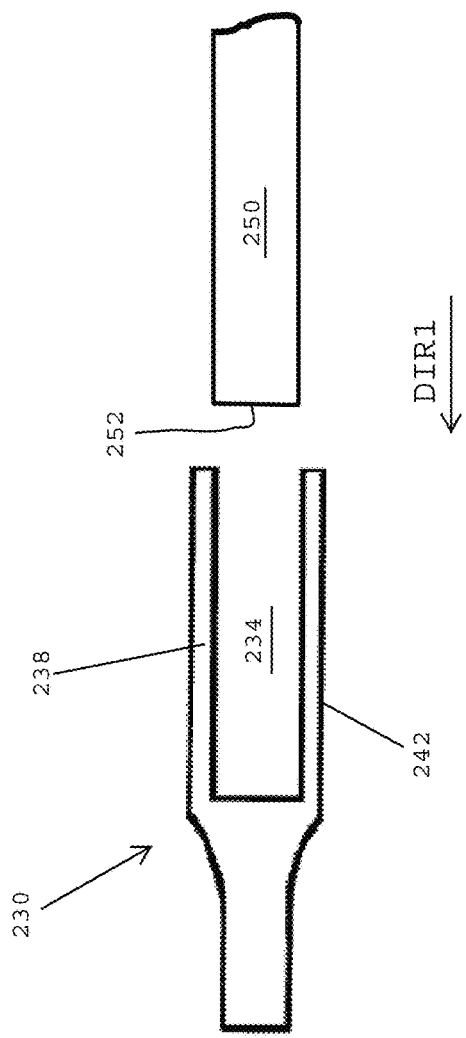
FIG. 9B shows a second step of a method of using the connector of FIGS. 8A-8B for coupling a suture with a surgical needle, in accordance with one embodiment of the present patent application.
Figure 9C:
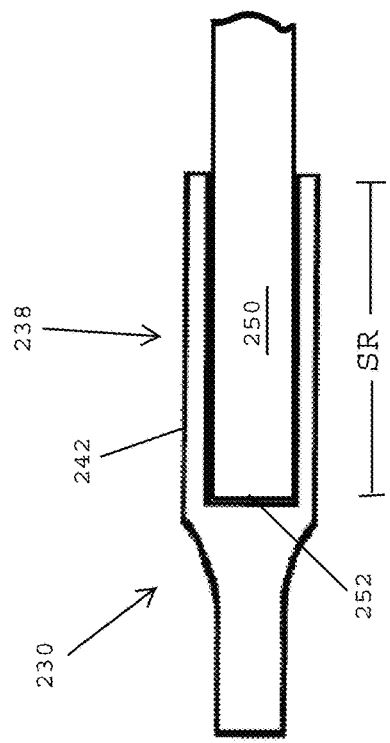
FIG. 9C shows a third step of a method of using the connector of FIGS. 8A-8B for coupling a suture with a surgical needle, in accordance with one embodiment of the present patent application.

Referring to FIGS. 9B and 9C, in one embodiment, the distal end 252 of the suture 250 is preferably advanced in the direction designated DIR1 for insertion into the opening 234 provided in the second section 238 of the connector 230. The outer surface 242 of the second section 238 of the connector 230 that overlies the distal end 252 of the suture 250, designated the swaged region SR, may be swaged, crimped, and/or deformed for clamping and/or securing the connector 230 to the distal end 252 of the suture 250.

Referring to FIG. 9D, in one embodiment, after the connector 230 has been secured to the end of the suture 250, the smaller diameter first section 236 of the connector may be inserted into the hole 214 provided at the proximal end 206 of the needle 200. Referring to FIGS. 9D and 9E, in one embodiment, the connector 230 is preferably advanced in the direction designated DIR1 so that the first section 236 of the connector is inserted into the hole 214 of the needle 200 for securing the connector 230 and the suture 250 to the needle 200.

Figure 10A:
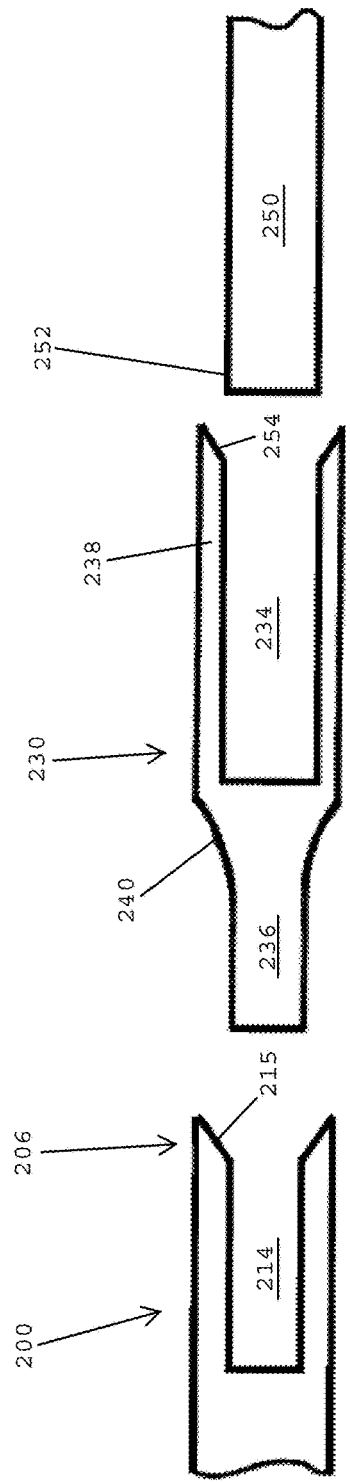
FIG. 10A shows a first step of a method of using a connector for coupling a suture with a surgical needle, in accordance with one embodiment of the present patent application.
Figure 10B:
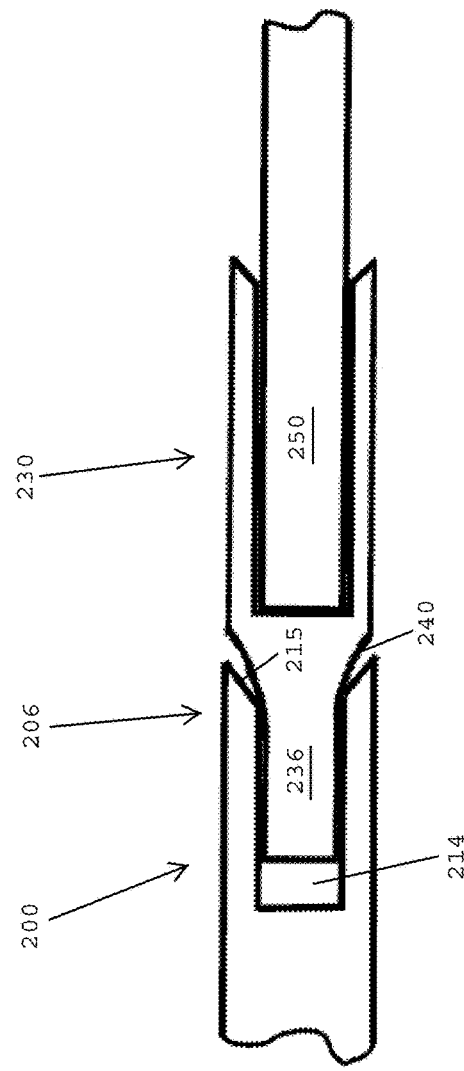
FIG. 10B shows a second step of a method of using a connector for coupling a suture with a surgical needle, in accordance with one embodiment of the present patent application.

Referring to FIG. 10A, in one embodiment, the opening 234 formed in the second section 238 of the connector 230 may include a tapered surface 254 that extends around the opening 234 to preferably minimize any frictional engagement with the suture 250 as the distal end 252 of the suture 250 is inserted into the opening 234 of the connector 230. The tapered surface 254 preferably minimizes the potential for any damage being caused to the suture 250 as the suture is inserted into the opening 234 of the connector 230.

In one embodiment, the hole 214 formed at the proximal end 206 of the needle 200 may include a tapered surface 215 that conforms to the sloping surface 240 that extends between the first section 236 and the second section 238 of the connector 230. The sloping surface 240 preferably facilitates alignment and insertion of the first section 236 of the connector 230 into the hole 214 located at the proximal end 206 of the needle 200. In addition, the opposing tapered surface 215 of the needle 200 and the sloping surface 240 of the connector 230 desirably provide additional surface area where the needle and the connector engage one another for effectively securing the connector 230 to the proximal end 206 of the needle 200.

Figure 11:
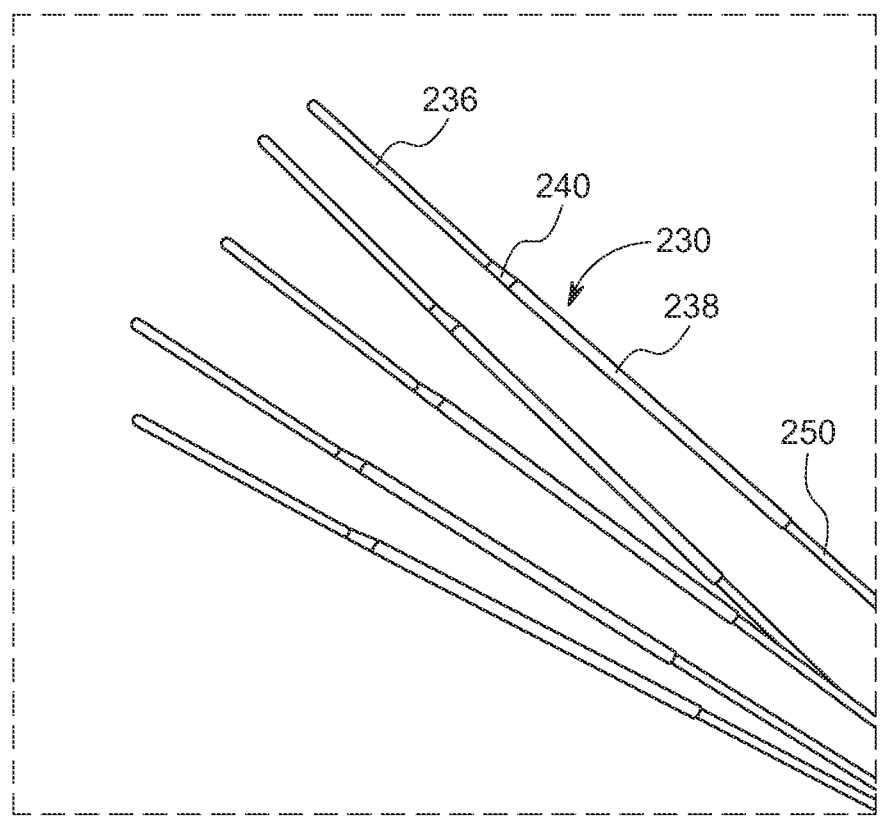
FIG. 11 is a perspective view of connectors having proximal ends secured to distal ends of sutures, in accordance with one embodiment of the present patent application.

Referring to FIG. 11, in one embodiment, a connector 230 as shown and described above in FIGS. 8A-10B, may be secured to a distal end of suture 250. In FIG. 11, the connector 230 includes that first section 236 having a smaller outer diameter, the second section 238 having a larger outer diameter than the first section, and the sloping surface 240 that extends from the first section to the second section. A free or distal end of the suture 250 is preferably inserted into the opening 234 (FIG. 9) provided in the larger diameter second section 238 of the connector 230. After the suture 250 is advanced into the opening, the second section 238 of the connector 230 may be swaged for securing the connector to the end of the suture 250. In FIG. 11, five individual sutures are secured to five different connectors 230.

Figure 12:
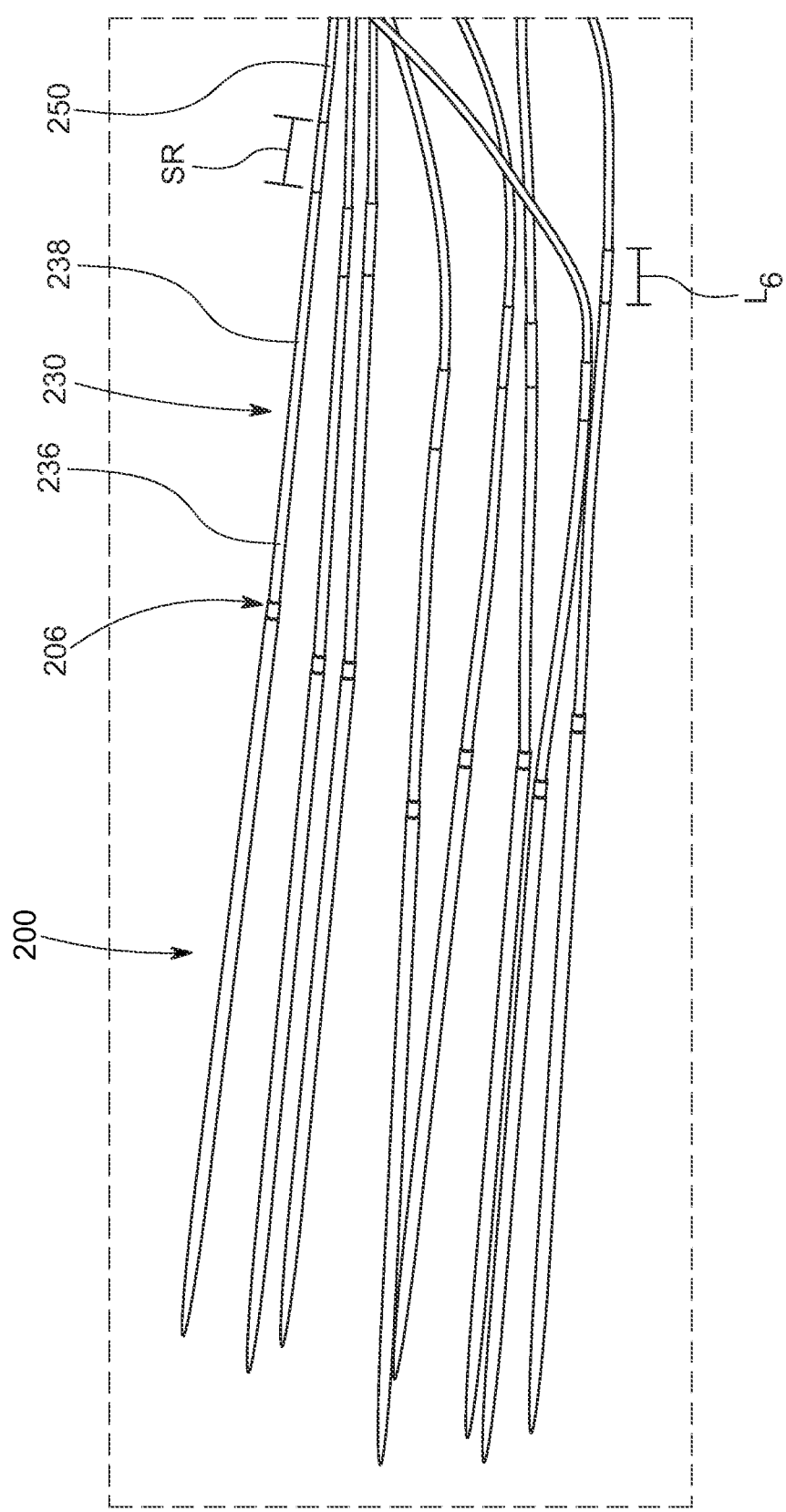
FIG. 12 shows the distal ends of the connectors of FIG. 11 being secured to proximal ends of surgical needles, in accordance with one embodiment of the present patent application.

Referring to FIG. 12, in one embodiment, after the suture 250 has been secured to the second section 238 of the connector 230, the smaller diameter first section 236 of the connector 230 is preferably inserted into the hole 214 (FIG. 7A) provided at the proximal end 206 of the needle 200. In one embodiment, each connector 230 desirably includes a sloping surface 240 where the outer surface of the connector 230 slopes outwardly between the smaller diameter first section 236 and the larger diameter second section 238. As shown in FIG. 12, a portion of the length of the second end 238 is swaged within a swaged region SR for securing the connector 230 to the end of the suture 250. In one embodiment, the swaged region may have a length $L_6$.

Figure 13A:
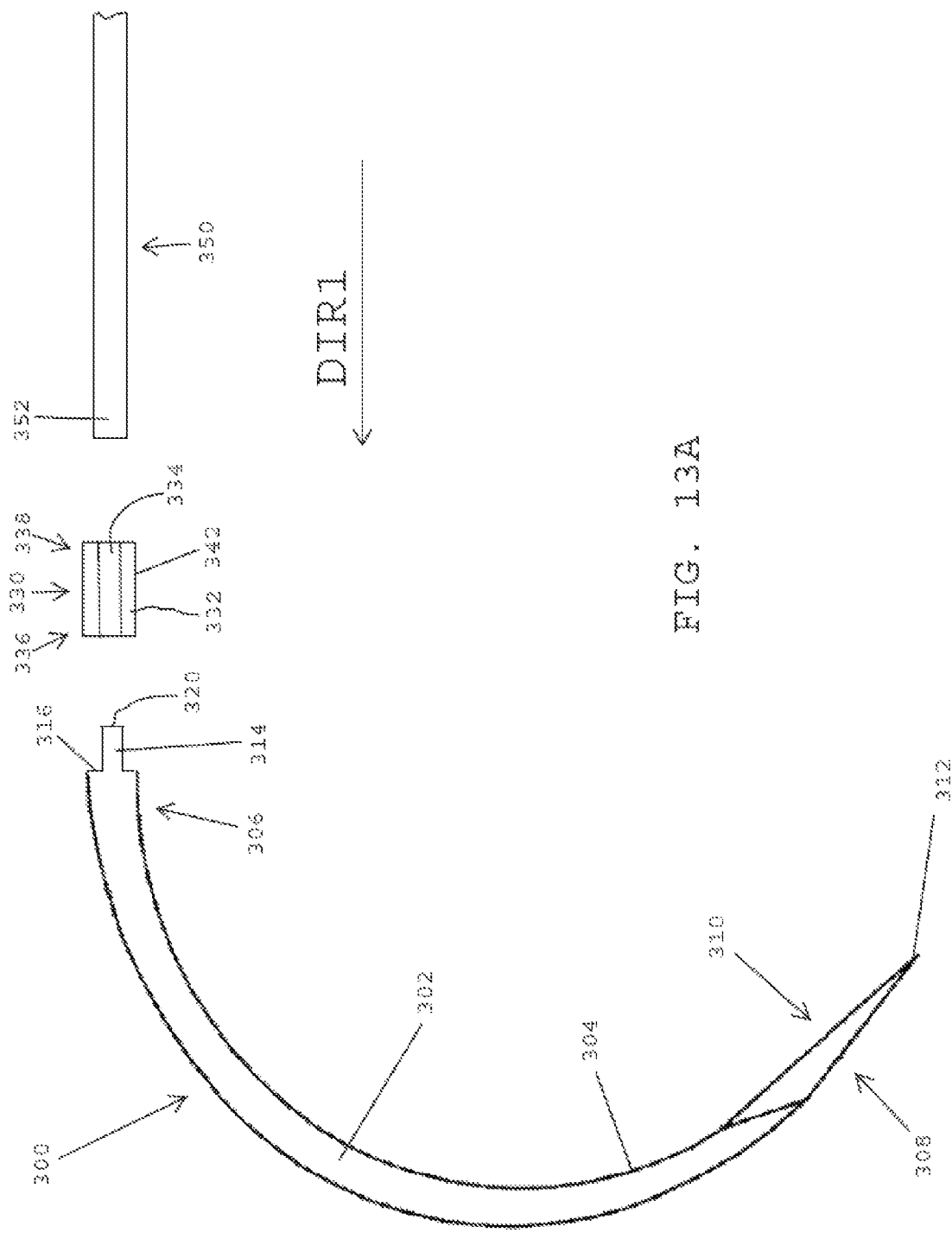
FIG. 13A shows a first step of a method of using a tubular connector for securing a suture to a curved surgical needle, in accordance with one embodiment of the present patent application.

Referring to FIG. 13A, in one embodiment, a curved needle 300, preferably made of a superelastic alloy or having shape memory properties, has an elongated body 302 with an outer surface 304 that extends along the length of the needle. In one embodiment, the elongated body 302 preferably has a proximal end 306 and a distal end 308 having a tapered region 310 that terminates at a sharpened tip 312, which is located at a distal-most end of the needle 300. In one embodiment, the needle 300 desirably includes an attachment post 314 that preferably projects proximally from the proximal end 306 of the elongated body 302 of the needle 300.

Referring to FIGS. 13A and 13B, in one embodiment, a connector 330, similar to that shown and described above in FIGS. 4A-4C, may be utilized for connecting a suture 350 with the needle 300. In one embodiment, the connector 330 desirably includes the tubular body 332 having a tubular shape with a first end 336 and a second end 338. The connector has an elongated conduit 334 that desirably extends along the length of the connector 330 and provides openings at the respective first and second ends 336, 338 of the tubular body.

In one embodiment, a distal end 352 of the suture 350 is desirably positioned adjacent the second end 338 of the tubular body 332 of the connector. The distal end 352 of the suture 350 is preferably aligned with an opening located at the second end 338 of the tubular member 332, which is aligned with the elongated conduit 334. In one embodiment, the suture is desirably advanced in the direction designated DIR1 so that the distal end 352 of the suture 350 is positioned within the conduit 334 of the tubular body 332.

In one embodiment, after the distal end 352 of the suture 350 is positioned inside the tubular body 332 of the connector 330, the outer surface 342 of the tubular body 332 overlying the suture may be swaged or crimped for deforming the tubular body 332 to secure the connector 330 to the distal end 352 of the suture 350. The region of the connector 330 that surrounds the suture 350 is desirably swaged for forming a secure connection between the suture 350 and the connector 330.

In one embodiment, after the connector 330 has been secured to an end of the suture 350, the attachment post 314 projecting from the proximal end 306 of the elongated body 302 of the needle 300 may be aligned with the elongated conduit 334 at the first end 336 of the tubular body 332 of the connector 330. The connector 330 is preferably advanced over the attachment post 314 of the needle 300 in the direction designated DIR1 until the first end 336 of the tubular body 332 abuts against the proximal end face 316 located at the proximal end 306 of the elongated body 302 of the needle 300. In one embodiment, the distal end 320 of the attachment post 314, disposed within the tubular body 332 of the connector 330, may abut against the distal end 352 of the suture 350.

Figure 14A:
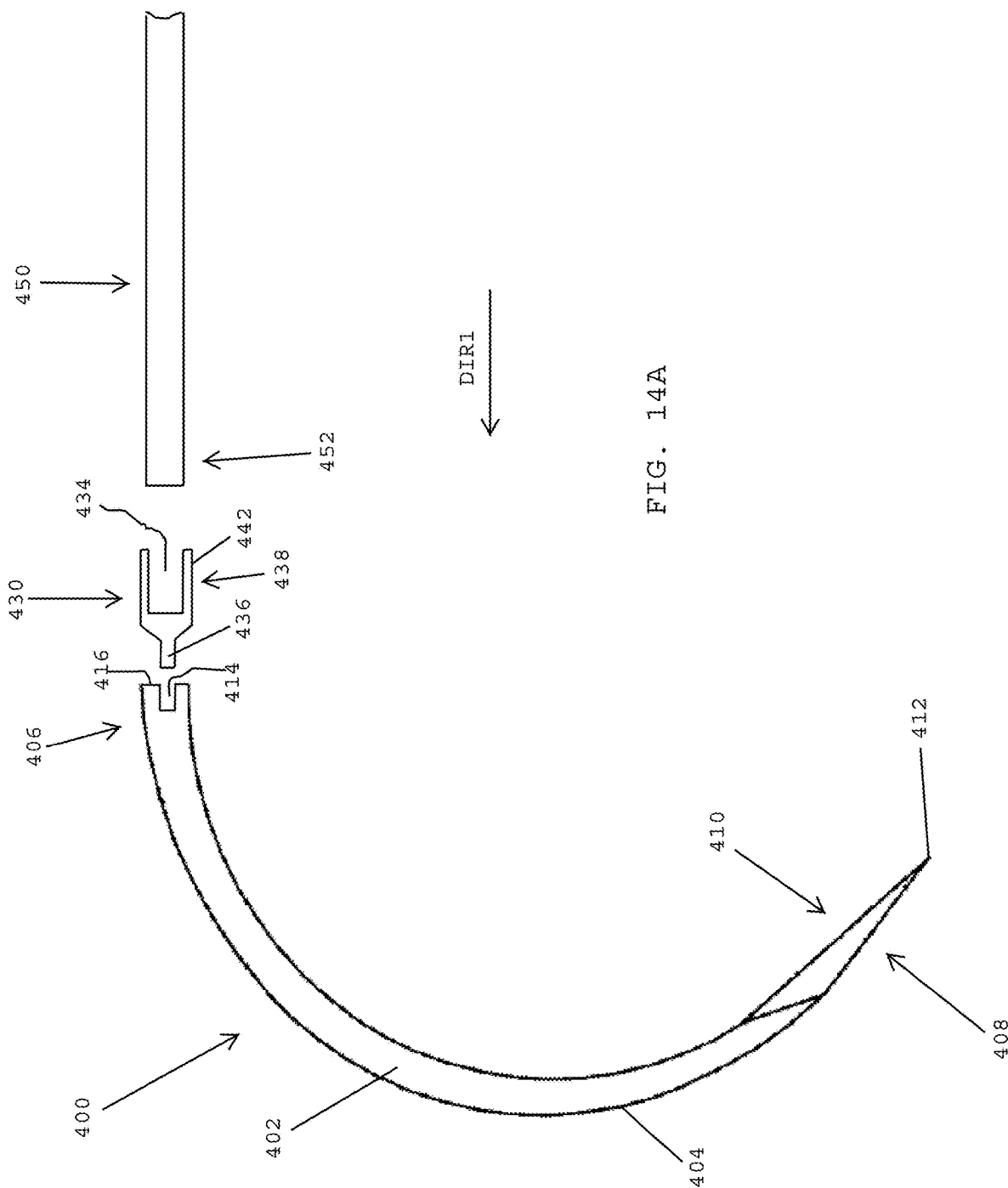
FIG. 14A shows a first step of a method of using a connector for securing a suture to a curved surgical needle, in accordance with one embodiment of the present patent application.

Referring to FIGS. 14A and 14B, in one embodiment, a curved needle 400, such as a needle made of a superelastic alloy or having shape memory properties, preferably includes an elongated body 402 having an outer surface 404 that extends along the length of the needle. The curved needle 400 preferably has a proximal end 406 and a distal end 408 including a tapered region 410, at the distal end 410 of the needle, which terminates at a sharpened tip 412 that defines a distal-most end of the needle. In one embodiment, the curved needle 400 preferably includes a hole 414 (e.g., a drilled hole or opening) that is desirably formed in a proximal end face 416 of the elongated body 402.

In one embodiment, a connector 430, such as a stainless steel connector having less elasticity and greater plasticity than the curved needle 400, is used for coupling a suture with the curved needle 400. The connector 430 preferably has a first section 436 that defines a smaller diameter region of the connector and a second section 438 that defines a larger diameter region of the connector. In one embodiment, the outer surface of the connector 430 preferably has a sloping surface 440 that extends from the smaller diameter first section 436 to the larger diameter second section 438.

In one embodiment, the connector 430 may be utilized for securing a distal end 452 of a suture 450 to the proximal end 406 of the curved needle 400. In one embodiment, the distal end 452 of the suture 450 is preferably advanced in the direction designated DIR1 for insertion into an opening 434 provided in the second section 438 of the connector 430. After the end of the suture 450 is inserted into the opening 434 of the connector 430, the outer surface 442 of the second section 438 of the connector 430 that overlies the distal end 452 of the suture 450 may be swaged, crimped, and/or deformed for clamping and/or securing the connector 430 to the distal end 452 of the suture 450.

In one embodiment, after the connector 430 has been secured to the end of the suture 450, the smaller diameter first section 436 of the connector may be inserted into the hole 414 provided at the proximal end 406 of the needle 400. In one embodiment, the connector 430 is preferably advanced in the direction designated DIR1 so that the first section 436 of the connector is inserted into the hole 414 of the needle 400 for securing the connector 430 and the suture 450 to the curved needle 400.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A needle and suture assembly comprising:
    a curved needle made of a superelastic alloy, said needle including an elongated body having a proximal end and a distal end with a sharpened tip;
    a suture having a free end juxtaposed with the proximal end of said elongated body of said needle;
    a metallic connector disposed between said needle and said suture, said connector including a first end attached to the proximal end of said elongated body of said needle and a second end attached to the free end of said suture, wherein said connector is made of a material having greater plasticity than said superelastic alloy of said needle;
    wherein said needle further comprises an attachment post projecting from the proximal end of said elongated body, said attachment post having a length that extends along a longitudinal axis, and wherein said attachment post has a lateral surface that extends along the length of said attachment post and that slopes inwardly between a proximal end and a distal end of said attachment post at an angle of one degree relative to the longitudinal axis of said attachment post.

2. The assembly as claimed in claim 1, wherein said superelastic alloy comprises Nitinol, and wherein said connector comprises stainless steel.

3. The assembly as claimed in claim 2, wherein said stainless steel comprises austenitic stainless steel and 316 stainless steel.

4. The assembly as claimed in claim 1, wherein said elongated body of said needle has a first cross-sectional diameter and said attachment post has a second cross-sectional diameter that is smaller than the first cross-sectional diameter of said elongated body.

5. The assembly as claimed in claim 4, wherein said attachment post comprises:
    the distal end secured to a proximal end face of said elongated body, the distal end of said attachment post having a first outer diameter;

the proximal end spaced from the distal end of said attachment post that defines a proximal-most end of said needle, the proximal end of said attachment post having a second outer diameter that is greater than the first outer diameter at the distal end of said attachment post.

6. The assembly as claimed in claim 4, further comprising:
said metallic connector including a tubular body having a conduit that extends from a first opening at a first end of said tubular body to a second opening at a second end of said tubular body;
said attachment post being inserted into the first opening at the first end of said tubular body and extending into said conduit for securing said tubular body with said attachment post of said needle;
the free end of said suture being inserted into the second opening at the second end of said tubular body and extending into said conduit for securing said tubular body to the free end of said suture.

7. The assembly as claimed in claim 6, wherein the second end of said tubular body is swaged for pinching the free end of said suture extending into said conduit of said tubular body.

8. The assembly as claimed in claim 6, wherein the first end of said tubular body is swaged for securing the first end of said tubular body to said attachment post of said needle.

9. The assembly as claimed in claim 6, wherein the first end of said tubular body forms an interference fit or a compression fit with said attachment post of said needle.

10. A needle and suture assembly comprising:
a curved Nitinol needle including an elongated body having a proximal end and a distal end with a sharpened tip;
a suture having a free end juxtaposed with the proximal end of said elongated body of said Nitinol needle;
a stainless steel connector disposed between said Nitinol needle and said suture, said stainless steel connector including a first end attached to the proximal end of said elongated body of said Nitinol needle and a second end attached to the free end of said suture, wherein said Nitinol needle has greater elasticity than said stainless steel connector, and wherein said stainless steel connector has greater plasticity than said Nitinol needle;
wherein said Nitinol needle further comprises an attachment post projecting from the proximal end of said elongated body, said attachment post having a length that extends along a longitudinal axis, and wherein said attachment post has a lateral surface that extends along the length of said attachment post and that slopes inwardly between a proximal end and a distal end of said attachment post at an angle of one degree relative to the longitudinal axis of said attachment post.

11. The assembly as claimed in claim 10, wherein said elongated body of said needle has a first cross-sectional diameter and said attachment post of said needle has a second cross-sectional diameter that is smaller than the first cross-sectional diameter of said elongated body.

12. The assembly as claimed in claim 11, wherein said attachment post comprises:
the distal end secured to a proximal end face at the proximal end of said elongated body of said needle, the distal end of said attachment post having a first outer diameter;
the proximal end spaced from the distal end of said attachment post that defines a proximal-most end of said needle, the proximal end of said attachment post having a second outer diameter that is greater than the first outer diameter at the distal end of said attachment post.

13. The assembly as claimed in claim 12, further comprising:
said connector including a tubular body having an elongated conduit that extends from a first opening at a first end of said tubular body to a second opening at a second end of said tubular body;
said attachment post being inserted into the first opening at the first end of said tubular body and extending into said elongated conduit for securing the first end of said tubular body with said attachment post of said needle;
said free end of said suture being inserted into the second opening at the second end of said tubular body and extending into said elongated conduit for securing said tubular body to the free end of said suture.

14. The assembly as claimed in claim 13, wherein the first end of said tubular body includes a first swage region securing the first end of said tubular body to said attachment post of said needle, and wherein the second end of said tubular body includes a second swage region for securing the second end of said tubular body to the free end of said suture.

15. The assembly as claimed in claim 13, wherein the first end of said tubular body forms an interference fit or a compression fit with said attachment post of said needle.

16. A needle and suture assembly comprising:
a curved surgical needle made of a superelastic alloy, said curved surgical needle including an elongated body having a proximal end and a distal end with a sharpened tip;
a suture having a free end juxtaposed with the proximal end of said elongated body of said curved surgical needle;
a connector disposed between said needle and said suture, said connector including a first end attached to the proximal end of said elongated body of said curved surgical needle and a second end attached to the free end of said suture, wherein said connector is made of a material having less elasticity and greater plasticity than said superelastic alloy of said curved surgical needle;
wherein said elongated body of said curved surgical needle further comprises a hole with a tapered surface formed in a proximal end face of said elongated body, wherein the first end of said connector comprises a wire that is inserted into said hole with the tapered surface formed in the proximal end face of said elongated body for securing the first end of said connector with the proximal end of said elongated body, and wherein the second end of said connector comprises a tubular member having an opening that seats the free end of said suture for securing the connector to the free end of said suture;
wherein the first end of said connector defines a smaller diameter region of said connector and the second end of said connector defines a larger diameter region of said connector, and wherein said connector has an outer surface that slopes outwardly from said smaller diameter first section of said connector to said larger diameter second section of said connector, and wherein said tapered surface of said hole at the proximal end of said elongated body conforms to said sloping outer surface of said connector for securing said connector to the proximal end of said elongated body of said needle.

17. The assembly as claimed in claim 16, wherein said opening in said tubular member of said connector that seats the free end of said suture has a tapered surface that extends around said opening.

\* \* \* \* \*